US011394296B2

(12) United States Patent
Lee

(10) Patent No.: US 11,394,296 B2
(45) Date of Patent: Jul. 19, 2022

(54) VOLTAGE DRIVER FOR ELECTROWETTING LENS

(71) Applicant: Verily Life Sciences LLC, Mountain View, CA (US)

(72) Inventor: Shungneng Lee, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 425 days.

(21) Appl. No.: 16/147,613

(22) Filed: Sep. 29, 2018

(65) Prior Publication Data

US 2019/0109536 A1 Apr. 11, 2019

Related U.S. Application Data

(60) Provisional application No. 62/570,751, filed on Oct. 11, 2017.

(51) Int. Cl.
*A61F 2/16* (2006.01)
*H02M 3/07* (2006.01)
(Continued)

(52) U.S. Cl.
CPC ............. *H02M 3/07* (2013.01); *A61F 2/1627* (2013.01); *A61F 2/1635* (2013.01); *G02B 3/14* (2013.01); *G02B 26/005* (2013.01); *H02M 3/071* (2021.05)

(58) Field of Classification Search
None
See application file for complete search history.

(56) References Cited

U.S. PATENT DOCUMENTS 5,364,801 A * 11/1994 Smayling ............... H01L 27/115
257/E21.68
9,553,527 B1 1/2017 Ramos et al.
(Continued)

FOREIGN PATENT DOCUMENTS

| EP | 2648031 A1 | 10/2013 |
| EP | 3185419 A1 | 6/2017 |
| JP | 2013218326 A | 10/2013 |

OTHER PUBLICATIONS

International Search Report of International Application No. PCT/US2018/053904, dated Jan. 2, 2019.

*Primary Examiner* — Leslie Lopez
(74) *Attorney, Agent, or Firm* — McDonnell Boehnen Hulbert & Berghoff LLP

(57) ABSTRACT

A voltage driver can be operated to power an electrowetting lens of an eye-implantable or eye-mountable device. The voltage driver includes a first charge pump that outputs a first voltage having a first polarity and a second charge pump that outputs a second voltage having a second polarity, where the second polarity is an opposite polarity of the first polarity. The voltage driver can be operated to charge the electrowetting lens by coupling the first charge pump to the electrowetting lens and, after charging the electrowetting lens, discharge the electrowetting lens by coupling the second charge pump to the electrowetting lens. In operation, charging and discharging the electrowetting lens adjusts an optical power of the electrowetting lens and can thus adjust an optical power available for vision when the electrowetting lens is implanted in or mounted on an eye.

18 Claims, 12 Drawing Sheets

(51) Int. Cl.
*G02B 3/14* (2006.01)
*G02B 26/00* (2006.01)

(56) References Cited

U.S. PATENT DOCUMENTS

| | | |
|---|---|---|
| 2007/0153405 A1 | 7/2007 | Kuiper et al. |
| 2009/0110384 A1 | 4/2009 | Lynch et al. |
| 2010/0110532 A1 | 5/2010 | Takemoto et al. |
| 2010/0308890 A1 | 12/2010 | Schlueter et al. |
| 2013/0079763 A1* | 3/2013 | Heckel ............... A61B 18/1206 606/33 |
| 2013/0258275 A1* | 10/2013 | Toner ............... G02C 7/083 351/159.03 |
| 2013/0278232 A1* | 10/2013 | Herbison ............... H02M 3/157 323/234 |
| 2017/0063351 A1 | 3/2017 | Yoshiyuki |
| 2017/0176773 A1 | 6/2017 | Whitney et al. |

\* cited by examiner

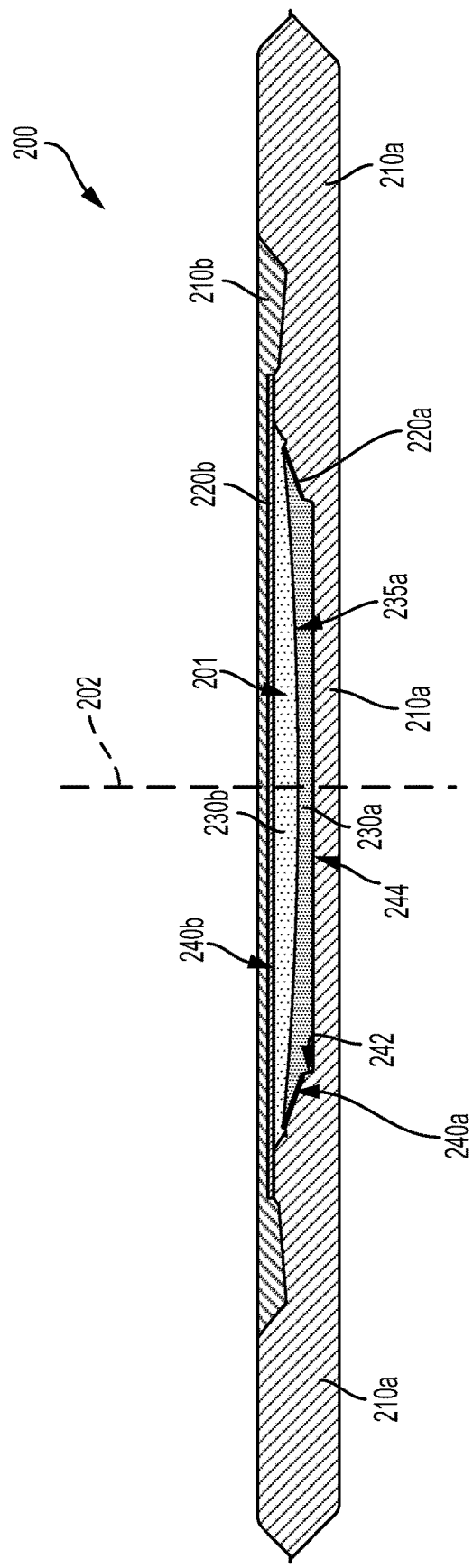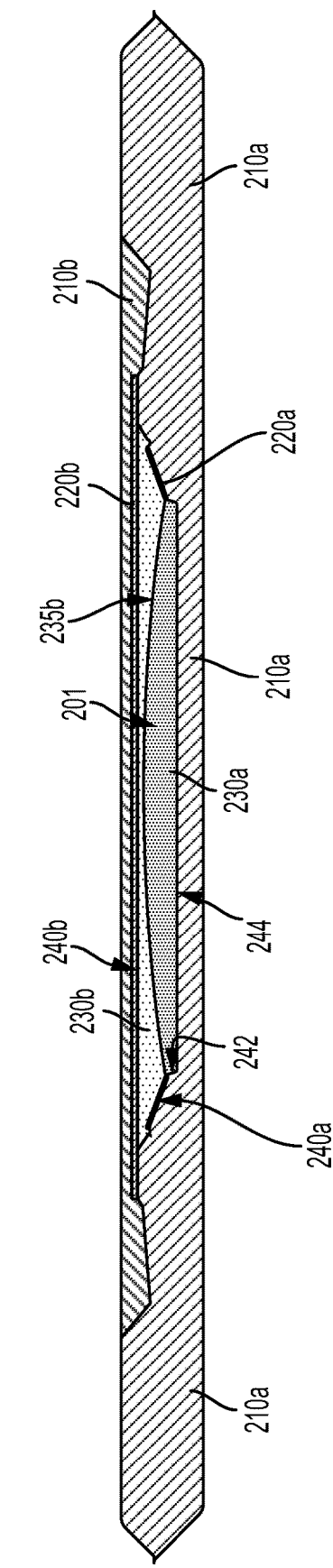

US 11,394,296 B2

VOLTAGE DRIVER FOR ELECTROWETTING LENS

CROSS-REFERENCE TO RELATED APPLICATION

This application claims priority to U.S. Provisional Patent Application No. 62/570,751, filed Oct. 11, 2017, which is incorporated herein by reference.

BACKGROUND

Unless otherwise indicated herein, the materials described in this section are not prior art to the claims in this application and are not admitted to be prior art by inclusion in this section.

Devices can be provided on the surface of the eye and/or within the eye to provide a variety of functions. In some examples, these functions can include functions to improve the ability of a person to view their environment (e.g., to provide an optical correction, to stimulate the retina directly) and/or to present additional visual information to the person (e.g., to present a heads up display or other indications to the person). Additionally or alternatively, these functions can include detecting a property of the body of a person (e.g., a blood glucose level, a concentration of an ion in the blood, a desired optical power of the eye) via the eye, e.g., by detecting forces, concentrations of analytes, electrical fields, or other properties related to the property of interest. Such functions can be provided by an intraocular device implanted within the eye (e.g., a retinal implant configured to stimulate the retina to restore vision, a device implanted within the lens capsule to provide a static and/or controllable optical power to the eye).

SUMMARY

Some embodiments of the present disclosure provide a system that includes an electrowetting lens; a first charge pump that outputs a first voltage having a first polarity; a second charge pump that outputs a second voltage having a second polarity, wherein the second polarity is an opposite polarity of the first polarity; and a controller. The controller is operable to (i) charge the electrowetting lens by coupling the first charge pump to the electrowetting lens and (ii) after charging the electrowetting lens, discharge the electrowetting lens by coupling the second charge pump to the electrowetting lens, wherein charging and discharging the electrowetting lens adjusts an optical power of the electrowetting lens.

Some embodiments of the present disclosure provide an eye-implantable device that includes an electrowetting lens; a first charge pump that outputs a first voltage having a first polarity; a second charge pump that outputs a second voltage having a second polarity, wherein the second polarity is an opposite polarity of the first polarity; and a controller. The electrowetting lens includes a first fluid disposed in the lens, wherein the first fluid comprises an aqueous solution having an osmolality corresponding to an osmolality of an aqueous humor of a human eye; a second fluid disposed in the lens, wherein the second fluid is immiscible with the first fluid, and wherein a refractive index of the second fluid differs from a refractive index of the first fluid; a first electrode in contact with the first fluid; and a second electrode in contact with at least one of the first fluid or the second fluid. The controller is operable to (i) charge the electrowetting lens by coupling the first charge pump to the electrowetting lens and (ii) after charging the electrowetting lens, discharge the electrowetting lens by coupling the second charge pump to the electrowetting lens, wherein charging and discharging the electrowetting lens adjusts an optical power of the electrowetting lens.

Some embodiments of the present disclosure provide a method including: (i) charging an electrowetting lens by coupling an output of a first charge pump to the electrowetting lens, wherein the first charge pump outputs a first voltage having a first polarity; and (ii) after charging the electrowetting lens, discharging the electrowetting lens by coupling an output of a second charge pump to the electrowetting lens, wherein the second charge pump outputs a second voltage having a second polarity that is an opposite polarity of the first polarity, and wherein charging and discharging the electrowetting lens adjusts an optical power of the electrowetting lens.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A is a side cross-section view of an example eye-implantable device during a first period of time.

FIG. 2B is a side cross-section view of the example eye-implantable device of FIG. 2A during a second period of time.

DETAILED DESCRIPTION

Figure 1A:
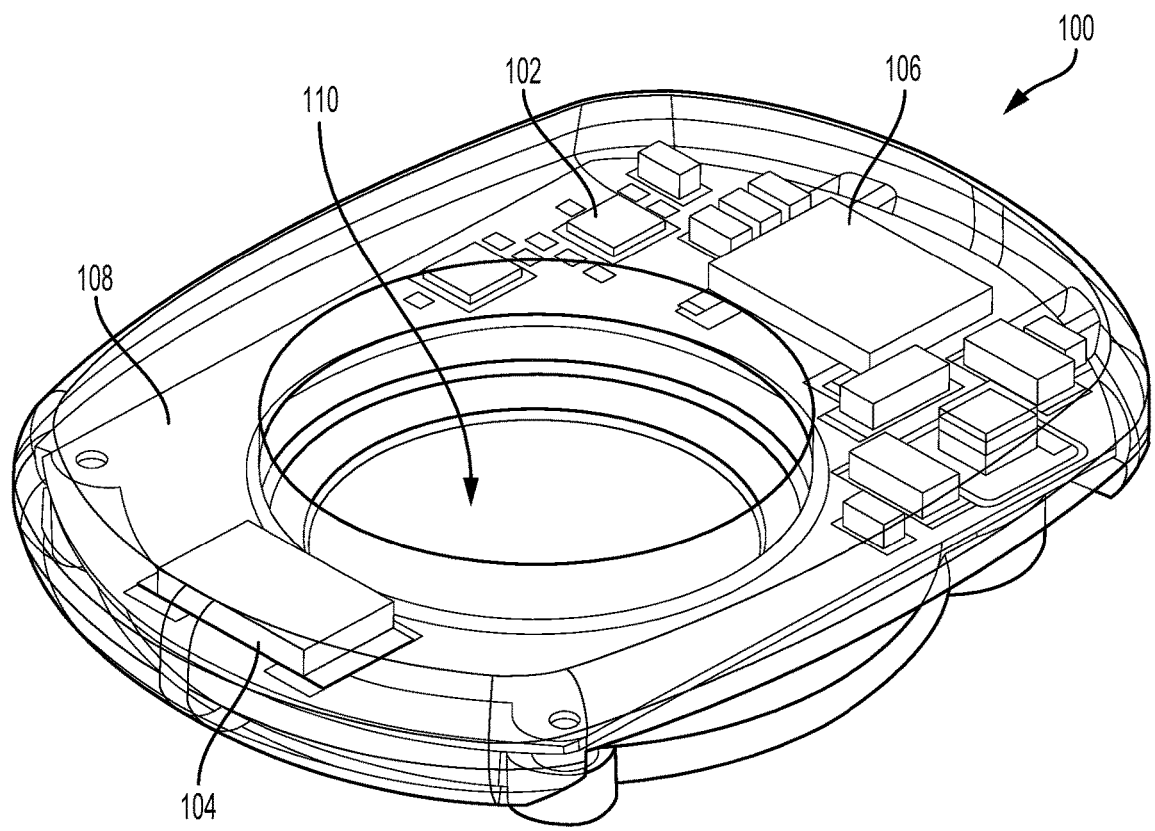
FIG. 1A is a perspective view of an example eye-implantable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Various applications may require a high voltage output from a low power circuit without sacrificing size constraints. CMOS processes may provide low power digital circuits in a small form factor but may have operating voltage limits that are less than 3V. Other semiconductor processes may be capable of supporting high voltages, but they may result in larger linewidth sizes and may not be well-characterized. Various boost-converters may be capable of generating high voltages, but they may involve the use of large, off-chip components to achieve higher efficiencies. As such, it can be difficult to produce high voltage outputs while minimizing power consumption and satisfying size constraints.

Example applications in which it may be desirable to produce a high voltage output from a low power circuit in a small form factor include eye-implantable and eye-mountable devices. Eye-implantable devices could be located within the eye of a person to provide a static or adjustable optical power to the eye, and eye-mountable devices could be mounted on a surface of the eye of a person to provide a static or adjustable optical power to the eye. Such a static or adjustable optical power could be provided to correct a lack or loss of optical power and/or accommodation in the eye, e.g., to correct for presbyopia, myopia, hyperopia, astigmatism, injury or damage to the eye, removal of the crystalline lens of the eye, or to correct for some other condition of the eye. These eye-implantable or eye-mountable devices could include an electronically actuated lens to provide a controllable amount of optical power to the eye. An electronically actuated lens could include an electrowetting lens that includes two or more immiscible fluids whose geometry within the electrowetting lens can be electronically controlled (e.g., by applying an electrical voltage to two or more electrodes of the lens) in order to control an overall optical power of the electrowetting lens.

Such eye-implantable or eye-mountable devices could include electronics, antennas, voltage regulators, batteries, photovoltaic cells, sensors, or other elements to facilitate operations of the device, e.g., to provide a controllable optical power to an eye. Such devices could receive radio frequency, optical, infrared, acoustic, or other forms of power to power the operations of the device, e.g., from a contact lens, eyeglasses, a head-mountable device, or some other source. The devices could receive wireless transmissions from an external device in the form of radio frequency, infrared, optical or other electromagnetic signals to specify an amount of optical power to provide, e.g., via an electrowetting lens. The devices could operate a sensor to detect a physical variable (e.g., an accommodation force exerted by ciliary muscles of the eye). The devices could use the detected physical variable to determine an amount of optical power to provide, or the devices could use some additional or alternative source of information or commands to determine an amount of optical power to provide to an eye.

The electronics of the eye-implantable or eye-mountable device can include a voltage driver that can be operated to adjust a voltage supplied to the electrowetting lens of the device. The voltage driver can include a first charge pump for pumping charge toward the electrowetting lens and a second charge pump for pumping charge away from the electrowetting lens. As such, the second charge pump can be coupled to the electrowetting lens in order to rapidly discharge the lens after the first charge pump has charged the lens.

The voltage driver can further include a voltage-sensing circuit for measuring and adjusting the output voltage of the first or second charge pumps. For instance, the voltage-sensing circuit can include a capacitive voltage divider for measuring the output voltage, as a capacitive voltage divider dissipates less power than a resistive voltage divider. However, because parasitic leakages of the voltage-sensing circuit may cause the voltage output of the capacitive voltage divider to drift over time, the voltage-sensing circuit can also include an additional capacitive voltage divider. The voltage-sensing circuit can then periodically switch between using the different capacitive voltage dividers to measure the output voltage in order to prevent voltage drift from interfering with the output of the voltage dividers. As such, the rate at which the voltage-sensing circuit switches between capacitive voltage dividers can depend on a charge leakage rate of one or more capacitors of the capacitive voltage dividers.

II. Example Eye-Implantable Device

An eye-implantable device (e.g., an intraocular lens, or IOL) can include electronics and an electronically actuated lens that are operable to provide a controllable optical power (e.g., a controllable diopter, focal length, or other form of optical power or refractive property) to an eye in which the device is implanted. Such an eye-implantable device could include haptics or other formed features, or be formed according to a particular shape, such that the eye-implantable device can be implanted in or at a particular location within an eye, e.g., within the lens capsule of the eye following removal of the crystalline lens, within the anterior chamber of the eye, within the posterior chamber of the eye, or along an optical axis of the eye. A controller, battery, antenna, sensors, or other elements can be provided to power the device, to determine a specified amount of optical power to provide to the eye (e.g., based on a sensor output or based on a received wireless command), and to operate the electronically actuated lens to provide such a specified optical power by applying a voltage, current, or other electrical signal to the electronically actuated lens. In some examples, the electronically actuated lens could be an electrowetting lens.

Figure 1B:
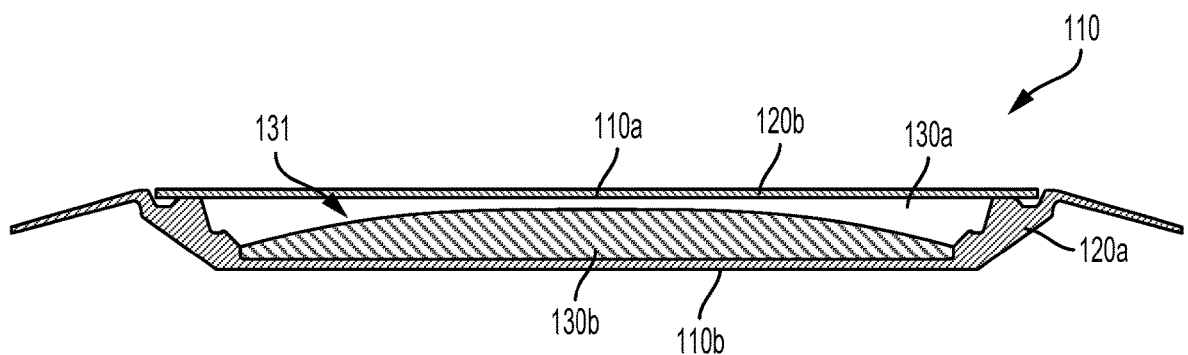
FIG. 1B is a side cross-section view of an electrowetting lens of the example eye-implantable device shown in FIG. 1A.

FIG. 1A is a perspective view of an example eye-implantable device 100. FIG. 1B is a cross-sectional view of an electrowetting lens 110 of the example eye-implantable device 100 shown in FIG. 1A. It is noted that relative dimensions in FIGS. 1A and 1B are not necessarily to scale, but have been rendered for purposes of explanation only in describing the arrangement of the example eye-implantable device 100 and electrowetting lens 110 thereof. The eye-implantable device 100 includes electronics arranged on a substrate 108 and configured to operate the electrowetting lens 110 to provide a controllable optical power and to provide other operations of the eye-implantable device 100. For instance, the electronics may include one or more controllers 102 for performing various functions to facilitate operation of the eye-implantable device 100, as described in further detail below, a driver circuit 104 for providing variable high voltage to the electrowetting lens 110 in order to control an optical power provided by the electrowetting lens 110, and a power source 106 (e.g., rechargeable batteries or the like) for powering the controller(s) 102, the driver circuit 104, and/or various other electronics of the eye-implantable device 100. Other electronics of the eye-implantable device 100 may include voltage regulators, antennas, photovoltaic cells, sensors, electrodes, transmitters, receivers, or other various components. The electronics may be configured to receive and/or store wireless energy to power the device 100 (e.g., visible light energy, infrared light energy, radio frequency electromagnetic energy, acoustic energy), to communicate with external devices or systems (e.g., to receive program updates, to receive a commanded optical power level), to detect one or more physical variables (e.g., a light level, a pupil diameter, an intraocular pressure, a voltage related to activity of muscles of the eye, a force exerted by ciliary muscles of the eye, a concentration of one or more substances in the eye) that may be used to determine an optical power to provide or that may be used in some other way, to operate the electrowetting lens 110, or to facilitate some other applications of the device 100.

The electrowetting lens 110 and/or other elements of the eye-implantable device 100 may be formed of one or more polymeric materials. The polymeric materials can include substantially transparent materials to allow incident light to be transmitted to the retina of the eye through the electrowetting lens 110 of the eye-implantable device 100. The polymeric materials can include biocompatible materials similar to those employed to form implants, vision correction lenses, IOLs, or other implantable devices, such as polyethylene terephthalate ("PET"), polymethyl methacrylate ("PMMA"), silicone hydrogels, rigid gas-permeable polymeric materials, combinations of these, etc. The polymeric materials could include flexible and/or foldable water-permeable materials. For example, the polymeric material could include a copolymer comprising 2-phenylethyl acrylate units and 2-phenylethyl methacrylate units. Units of a polymer or copolymer could be cross-linked by an applicable cross-linking agent or unit, e.g., by 1,4-butanediol diacrylate units, 1,6-hexanediol diacrylate units, or some other crosslinking agent or combination of such agents. Such flexible and/or foldable materials may be included in the construction of the device 100 to permit the device 100 to be rolled, folded, or otherwise manipulated such that the device 100 may be inserted through an incision that is smaller than, e.g., the diameter of the unrolled or un-folded electrowetting lens 110. The eye-implantable device 100 may include coating materials disposed on one or more external or internal surfaces of the device, e.g., to improve a biocompatibility of the device, to control a surface energy of an internal surface of the electrowetting lens (e.g., to encourage or prevent wetting of a surface within a lens chamber by one or more fluids within the lens chamber), to prevent to passage of ions or other substances, or to provide some other benefit.

The electrowetting lens 110 includes a lens chamber 131 in which are disposed a first fluid 130a and a second fluid 130b. The lens chamber 131 is formed from first 120a and second 120b elements shaped, respectively, as a cup and a flat lid. At least a portion of the first 120a and/or second 120b elements of the electrowetting lens 110 could be formed from a polymeric material (e.g., one of the polymeric materials listed elsewhere herein) that is permeable to water in the aqueous humor of an eye (e.g., from a copolymer comprising 2-phenylethyl acrylate units and 2-phenylethyl methacrylate units cross-linked by 1,4-butanediol diacrylate units). Such a water-permeable polymeric material, or other polymeric or non-polymeric materials of the electrowetting lens 110, could be flexible such that the electrowetting lens 110 can be rolled, folded, or otherwise manipulated, e.g., to facilitate insertion through an incision in an eye. Additionally or alternatively, one or more sealant materials (e.g., a sealant material used to adhere the first element 120a to the second element 120b) of the electrowetting lens 110 could be permeable to water in aqueous humor of an eye.

Note that the illustrated first 120a and second 120b elements of the chamber 131 of the electrowetting lens 110 are intended as non-limiting example embodiments. For example, an electrowetting lens and/or a lens chamber thereof as described herein could be constructed from more or fewer elements (e.g., from a front element, a rear element, and an annular element) than the two shown and/or could be constructed from elements configured differently from the elements 120a, 120b illustrated here.

The first 130a and second 130b fluids are immiscible (e.g., the first fluid 130a could be saline or some other aqueous fluid and the second fluid 130b could be an oil or some other nonpolar fluid) and differ with respect to refractive index. Thus, a surface of contact between the first 130a and second 130b fluids (e.g., a convex shape, as shown in FIG. 1B) could provide an optical power (e.g., a diopter, a nonzero focal length) related to the difference in the refractive indices of the fluids 130a, 130b and the shape of the surface of contact. The electrowetting lens 110 further includes at least two electrodes (shown in FIGS. 2A and 2B) disposed on respective internal surface of the lens chamber 131. Voltages, currents, or other electrical signals can be applied to the at least two electrodes to electronically control the shape of the first 130a and second 130b fluids (e.g., to control a shape of a contact surface between the two fluids 130a, 130b) in order to control an optical power of the electrowetting lens 110.

One of the first 130a or second 130b fluid may include an aqueous solution. Such an aqueous solution may be substantially isotonic relative to the aqueous humor of an eye into which the eye-implantable device 100 is implanted. The aqueous solution could have an osmolality corresponding to the osmolality of the aqueous humor such that, if the lens chamber is permeable to water in the aqueous humor, a small or substantially zero amount of net water flow occurs between the aqueous solution within the lens chamber and the aqueous humor of the eye. For example, the aqueous solution may have an osmolality greater than 297 milliosmoles per kilogram, such as between 300 milliosmoles per kilogram and 308 milliosmoles per kilogram. In another example, the aqueous fluid could have an osmolality between 302 milliosmoles per kilogram and 306 milliosmoles per kilogram.

The overall optical power provided by the eye-implantable device 100 and/or the electrowetting lens 110 (e.g., to an eye in which the device 100 is implanted) could be related to the geometry, refractive index, or other properties of the eye-implantable device 100. As noted above, this could include the shape of a contact surface between the first 130a and second 130b fluids within the lens chamber 131 and the refractive indices of the fluids 130a, 130b.

Other elements of the eye-implantable device 100 could provide a static and/or controllable optical power. For example, the front and/or rear surfaces of the electrowetting lens 110 could have curved surfaces to provide an optical power related to a change in refractive index between materials on either side of those surfaces (e.g., between a polymeric material of the first 120a and/or second 120b elements and aqueous humor of an eye, or between the polymeric material and one of the first 130a or second 130b fluids).

Components of the eye-implantable device 100 and/or electrowetting lens 110 (e.g., the first 120a or second 120b elements forming the lens chamber 131) can be formed to have a curved shape in a variety of ways. For example, techniques similar to those employed to form vision-correction contact lenses and/or intraocular lenses, such as heat molding, injection molding, spin casting, etc. can be employed to form polymeric materials into components of the eye-implantable device 100. Further, an eye-implantable device as described herein could have a different shape from that of the illustrated eye-implantable device 100. For example, an eye-implantable device could include haptics or other formed elements to maintain the eye-implantable device at a particular location within an eye (e.g., within a lens capsule of an eye), to detect accommodation forces exerted by ciliary muscles of an eye, or to provide some other benefit.

Figure 1C:
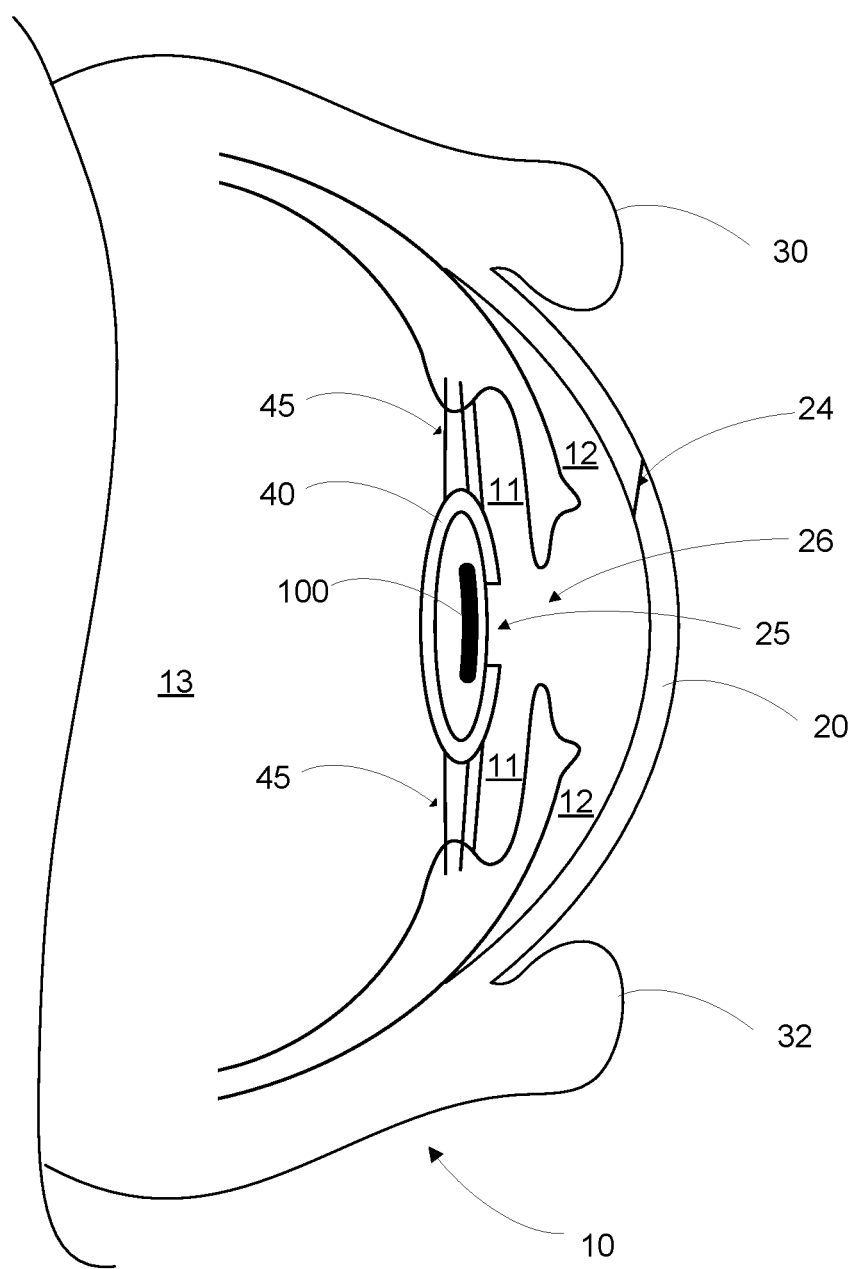
FIG. 1C is a side cross-section view of the example eye-implantable device shown in FIGS. 1A and 1B located within an eye.

FIG. 1C is a side cross-section view of the example eye-implantable device 100 while implanted within an eye 10. The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception.

In an unaltered eye, the light received by the retina is transmitted through the crystalline lens, being refracted by the lens such that light received from the environment arrives in focus at the retina. The crystalline lens is located within the lens capsule 40 of the eye, which is connected, via the zonules 45, to accommodation muscles (e.g., ciliary muscles) and other elements of the eye. Accommodation forces transmitted through the zonules 45 (e.g., forces generated by the accommodation muscles, forces generated by intrinsic elasticity of the zonules 45, or forces generated by other sources) act, in the eye, to deform the crystalline lens within the lens capsule 40, controlling the optical power provided by the crystalline lens.

As shown in FIG. 1C, however, the crystalline lens of the eye 10 has been removed from the lens capsule 40, and the eye-implantable device 100 has been surgically emplaced within the lens capsule 40, such that light received by the retina is transmitted through the electrowetting lens 110 of the eye-implantable device 100, causing the light to be refracted by the electrowetting lens 110 and/or other elements of the eye-implantable device 100. Thus, the eye-implantable device 100 can be operated such that light received from the environment may arrive in focus at the retina, e.g., by operating the electrowetting lens 110 to provide a specified optical power.

The eye-implantable device 100 can be inserted into the eye 10 through an incision 24 formed in the cornea 20 of the eye 10 and then positioned within the lens capsule 40. In order to position the device 100 within the lens capsule 40, a hole 25 can be formed in the lens capsule 40 (e.g., via continuous curvilinear capsulorhexis), the crystalline lens can be removed through the hole 25 (e.g., via ultrasonic phacoemulsification), and the device 100 can be inserted into the lens capsule 40 through the hole 25. An eye-implantable device as described herein may be positioned in alternative locations within the eye 10, e.g., within the posterior chamber 11, anterior chamber 12, or in the vitreous humor 13 of the eye 10.

It is noted that relative dimensions in FIG. 1C are not necessarily to scale, but have been rendered for purposes of explanation only in describing the arrangement of the example eye-implantable device 100 within the eye 10. Further, such an implanted device could include multiple elements, located, e.g., in multiple different locations. Such multiple elements could be connected via a cable or by some other means. For example, such an implanted device could include a power reception element and controller that is disposed in the posterior capsule 11 and that is operable to receive wireless power from an eye-mountable device or other external system (not shown) and an electrowetting lens that is disposed within the lens capsule 40 could be operated, by the controller, via a tether connecting the controller and the electrowetting lens, using power from the power reception element.

The eye-implantable device 100 may be rollable, foldable, or otherwise flexible to permit its being rolled, folded, or otherwise manipulated into a smaller shape. This could permit the device 100 to be inserted through a smaller incision through the cornea 20. For example, the device 100 could be rolled up, folded in half, folded in thirds, or manipulated in some other way to permit the device 100 to be inserted through an incision 24 that is less than four millimeters long. In some examples, the device 100 may be rollable, foldable, or otherwise manipulable such that it can be inserted through an incision 24 that is less than 2 millimeters long. In such examples, the eye-implantable device 100 may be unrolled, unfolded, or otherwise manipulated into an operation shape or state (e.g., a substantially flat state) after it is inserted through the incision 24 in the cornea 20 and/or after it has been inserted through some other formed hole or incision (e.g., the hole 25 in the lens capsule) or through some other opening or feature of the eye (e.g., the pupil 26 of the eye 10) to position the device 100 in a specified location of the eye 10.

Note that, while the electrowetting lens 110 is illustrated as containing two fluids 130a, 130b, an electrowetting lens as described herein could be manufactured and distributed containing only one fluid (e.g., a fluid that includes an aqueous solution having an osmolality corresponding to the osmolality of aqueous humor). A second fluid (e.g., an oil or other nonpolar fluid) could later be added to the electrowetting lens. Such an electrowetting lens containing only a single fluid could be provided to simplify implantation or fabrication of the electrowetting lens. For example, by folding such an electrowetting lens, inserting it into position in an eye, and unfolding the lens before addition of the second fluid, fouling and/or wetting of internal surfaces of the electrowetting lens by the second fluid (e.g., due to the second fluid contacting the internal surfaces as a result of folding, bending, or otherwise manipulating the electrowetting lens during implantation) can be avoided. The second fluid can then be added after the electrowetting lens has been unfolded (e.g., via injection through a septum of the electrowetting lens using a needle, via a tubule connected to the electrowetting lens).

An electrowetting lens (e.g., 110) as described herein may be configured in a variety of ways such that a shape of two or more fluids (e.g., a polar fluid and a nonpolar fluid) can be controlled by the application of a voltage, current, or other electrical signal to electrodes of the electrowetting lens. In some examples, this could include applying, via the electrodes, an electrical field that changes the effective surface energy, surface tension, interfacial energy, or other surface properties of one or more surfaces within a lens chamber of the electrowetting lens such that a first one of the immiscible fluids retreats or advances across the one or more surfaces. As the first fluid retreats or advances across the one or more surfaces, the overall shape of the first fluid, and of a contact surface between the first fluid and a second fluid that is immiscible with the first fluid, may change. If the first fluid and second fluid have differing refractive indices, light may be refracted when passing through the electrowetting lens and an amount of that refraction (and a corresponding optical power of the electrowetting lens) could be related to the shape of the contact surface. Thus, the overall optical power of the electrowetting lens can be electronically controlled by applying electrical signals to the electrodes of the electrowetting lens to, e.g., control the shape of one or more fluids within the electrowetting lens and/or to control a shape of a contact surface between such fluids of the electrowetting lens.

FIG. 2A illustrates a cross-sectional view of an example electrowetting lens 200 during a first period of time. The electrowetting lens 200 includes a lens chamber 201 define by first 210a and second 210b elements. In the example electrowetting lens 200, the lens chamber 201 is radially symmetric about a center line 202. A first electrode 220a is formed along a first internal surface 240a of the electrowetting lens 200 and takes the form of an inclined ring. A second electrode 220b is formed along a second internal surface 240b of the electrowetting lens 200. A first fluid 230a is disposed within the lens chamber 201 and, during the first period of time illustrated in FIG. 2A, is in contact with the first internal surface 240a, the first electrode 220a, a third internal surface 242 of the electrowetting lens 200, and a fourth internal surface 244 of the electrowetting lens 200. A second fluid 230b is also disposed within the lens chamber 201 and is, during the first period of time, in contact with the second internal surface 240b and the second electrode 220b. During the first period of time, a contact surface between the first fluid 230a and the second fluid 230b has a first shape 235a. The first 230a and second 230b fluids are immiscible (e.g., the first fluid 230a is a nonpolar fluid and the second fluid 230b is a polar fluid) and have differing refractive indices.

As the first 230a and second 230b fluids differ with respect to refractive index, light that passes through the contact surface (e.g., light that is passing through the electrowetting lens 200 along the center line 202) may be refracted. A degree or amount of the refraction, and a related optical power of the electrowetting lens 200, may be related to the shape of the contact surface between the first fluid 230a and the second fluid 230b The shape of the contact surface can be controlled by applying an electrical signal to the electrodes 220a, 220b, e.g., by applying an electrical voltage to the electrodes 240a, 240b. There could be a relationship between the voltage applied to the electrodes 240a, 240b and the steady-state (e.g., following any transient changes in the electrowetting lens resulting from changes in the applied voltage) optical power of the electrowetting lens 200 and/or the shape of the contact surface between the fluids 230a, 230b. Such a relationship could be related to an effect on the surface energy of the first internal surface 240a relative to each of the fluids 230a, 230b, to an effective capacitance between the first electrode 220a and the second electrode 220a via a conductive second fluid 230b (e.g., via a second fluid 230 that includes a conductive, aqueous solution and that is in conductive and/or capacitive electrical contact with the second electrode 220b), or to some other factors.

The first electrode 220a and second electrode 220b could include conductive materials (e.g., aluminum, gold, copper, or other materials) disposed on respective internal surfaces of the lens chamber 201 (e.g., on surfaces of the first element 210a and second element 210b, respectively). One or both of the electrodes could further include a dielectric layer disposed between such a conductive material and the inside of the lens chamber 201. For example, the first electrode 220a could include such a dielectric layer. Such a dielectric layer could be provided to prevent large, direct currents from passing from the first electrode 220a into one or both of the first 230a or second 230b fluids, to provide a capacitive electrical coupling between the first electrode 220a and such fluids, to limit an amount of charge that can be transmitting into such fluids via the first electrode 220a, or to provide some other benefits.

Such a dielectric layer could be a separate material (e.g., parylene) deposited on the conductive material (e.g., via CVD, spin coating, or some other process). Additionally or alternatively, the dielectric layer of the first electrode 220a could be formed from the conductive material of the electrode, e.g., the dielectric layer could be a nonconductive layer of aluminum oxide formed by oxidation of an underlying aluminum metal of the first electrode 220a. Such a dielectric layer could be formed via anodization or other electrically-driven reactions at the surface of the electrode. Additionally or alternatively, such a dielectric layer could be formed by redox reactions between the fluids in the lens chamber 201 and the material of the electrode.

In some examples, the formation and/or maintenance of such a dielectric layer could be negatively impacted by the presence of certain ions within the lens chamber 201 (e.g., dissolved in one or both of the fluids 230a, 230b). For example, the presence of chloride ions could act to pit or otherwise damage a dielectric layer of aluminum oxide that has formed on the surface of an aluminum electrode. In such examples, a barrier could be formed from a chloride-impermeable material to prevent chloride ions present in the aqueous humor (or in some other environment to which the lens 200 is exposed) from entering the lens chamber 201 or from entering some other material or volume of the lens 200. Such a material could include a polymeric material, a metal foil or deposited metal layer, or some other material(s). Such materials could be substantially transparent to visible light.

The voltage between the electrodes 220a, 220b could be controlled in order to control the optical power of the electrowetting lens 200 by controlling the shape of the contact surface between the fluids 230a, 230b. FIG. 2B illustrates the electrowetting lens 200 during a second period of time during which a voltage is being applied to the electrodes 220a, 220b such that the contact surface between the first fluid 230a and the second fluid 230b has a second shape 235b. As a result, the optical power of the electrowetting lens 200 during the second period of time is different than the optical power of the electrowetting lens 200 during the first period of time.

The particular shape of the contact surface and/or of the geometry of the fluids 230a, 230b could be related to the applied voltage and to a variety of other factors. Such factors could include the interfacial energy between the fluids 230a, 230b, the interfacial energy between the fluids 230a, 230b and the internal surfaces 240a, 240b, 242, 244, the geometry of the internal surfaces 240a, 240b, 242, 244, a geometry of the electrodes 220a, 220b, and/or a geometry of a dielectric layer of the first electrode 220a. One or more of these factors could be specified in order to affect the shape of the contact surface between the fluids 230a, 230b, to affect the geometry and/or location of the fluids 230a, 230b within the lens chamber 201, to affect the relationship between an applied voltage and the optical power of the electrowetting lens 200, or to affect some other property of interest of the electrowetting lens 200.

This could include adding surfactants, polar and/or ionic substances, nonpolar substances, to the fluid(s) or otherwise specifying a composition of the first 230a and/or second 230b fluids to control an interfacial energy between the fluids 230a, 230b and/or to control an interfacial energy between the fluids and the internal surfaces 240a, 240b, 242, 244 of the lens chamber. Additionally or alternatively, the composition of the material composing the internal surfaces 240a, 240b, 242, 244 could be specified to control the interfacial energy between the internal surfaces and the fluids.

This could include selecting the bulk materials of the first 210a and second 210b elements and/or providing one or more coatings or surface treatments to the internal surfaces of the lens chamber 201. For example, the first fluid 230a could be an oil or other nonpolar fluid and one or more of the first 240a, third 242, or fourth 244 internal surfaces could be superhydrophobic or otherwise hydrophobic. Further, the second fluid 230b could be a polar fluid (e.g., could include a saline solution or other aqueous solution having an osmolality corresponding to the osmolality of human aqueous humor) and the second 240b internal surface could be superhydrophilic or otherwise hydrophilic (e.g., by including a surface coating, by including a surface features or textures, by having been exposed to an oxidization process, or by some other means).

The distribution of such coatings or materials on the internal surfaces of the lens chamber 201 and/or the geometry of such surfaces could be specified to center the first fluid 230a along the center line 202 or along some other specified axis of the electrowetting lens 200. This could include applying different coating or other material to internal surfaces according to distance from the center line 202. Additionally or alternatively, a thickness or other property of a dielectric of the first electrode 220a could vary according to distance from the center line 202 such that, when a voltage is applied between the electrodes 220a, 220b, electrical and/or interfacial forces applied to the first 230a and/or second 230b fluids tend to center the first fluid 230a along the center line 202 and/or to conform a boundary between the fluids 230a, 230b on the first internal surface 240a to a circle centered on the center line 202.

The electrowetting lens 200 could be permeable to water or other substances (e.g., ions) in aqueous humor of an eye. This could include the electrowetting lens 200 being composed at least partially of a polymeric material that is permeable to water (or other substances) in the aqueous humor. In examples wherein the electrowetting lens 200 is permeable to a substance that is present in the aqueous humor, one or both of the fluids 230a, 230b could include a concentration of the substance corresponding to the concentration of the substance in the aqueous humor, e.g., to prevent a net flow of the substance from the aqueous humor into the lens chamber 201 or vice versa.

Additionally or alternatively, the electrowetting lens 200 could be made impermeable to such substances in the aqueous humor. This could include constructing the lens chamber 201 from materials that are impermeable to the substances. Additionally or alternatively, a barrier layer or coating could be formed from such impermeable materials to prevent the substances from entering the lens chamber 201 or some other element or structure of the electrowetting lens 200. For example, a barrier could be formed from a chloride-impermeable material to prevent chloride ions present in the aqueous humor from entering the lens chamber 201, or from entering some other material or volume of the lens 200. Such a material could include a polymeric material, a metal foil or deposited metal layer, or some other material(s). Such materials could be substantially transparent to visible light.

In some examples, components of the electrowetting lens 200 could be composed of a self-healing material. For example, the lens chamber 201 could be at least partially formed from self-healing materials. Such self-healing materials could be provided to maintain the integrity of the lens chamber 201 or of other volumes of the electrowetting lens 200 again bulk fluid flows into or out of such volumes (e.g., between the lens chamber 201 and the aqueous humor of an eye). In some examples, such self-healing materials may be degraded and/or their ability to self-heal diminished by exposure to chloride ions or other substances present in the aqueous humor and/or in the fluids 230a, 230b of the electrowetting lens 200. In such examples, an impermeable material (e.g., a chloride-impermeable material) could be used to form a barrier between the chloride ions or other substances present in the aqueous humor and the self-healing material.

III. Example Eye-Mountable Device

An eye-mountable device (e.g., a contact lens) can include an electronically actuated lens, such as an electrowetting lens (e.g., the electrowetting lens 200 depicted in FIGS. 2A and 2B), a driver circuit for driving the electronically actuated lens, one or more controller(s) for controlling the driver circuit, and a power source for powering the controller and the driver circuit. Such an eye-mountable device could be formed according to one of a variety of shapes such that the eye-mountable device can be removably mounted to an eye, e.g., the eye-mountable device could be shaped to mount to the cornea of the eye, over the pupil and iris.

Figure 3A:
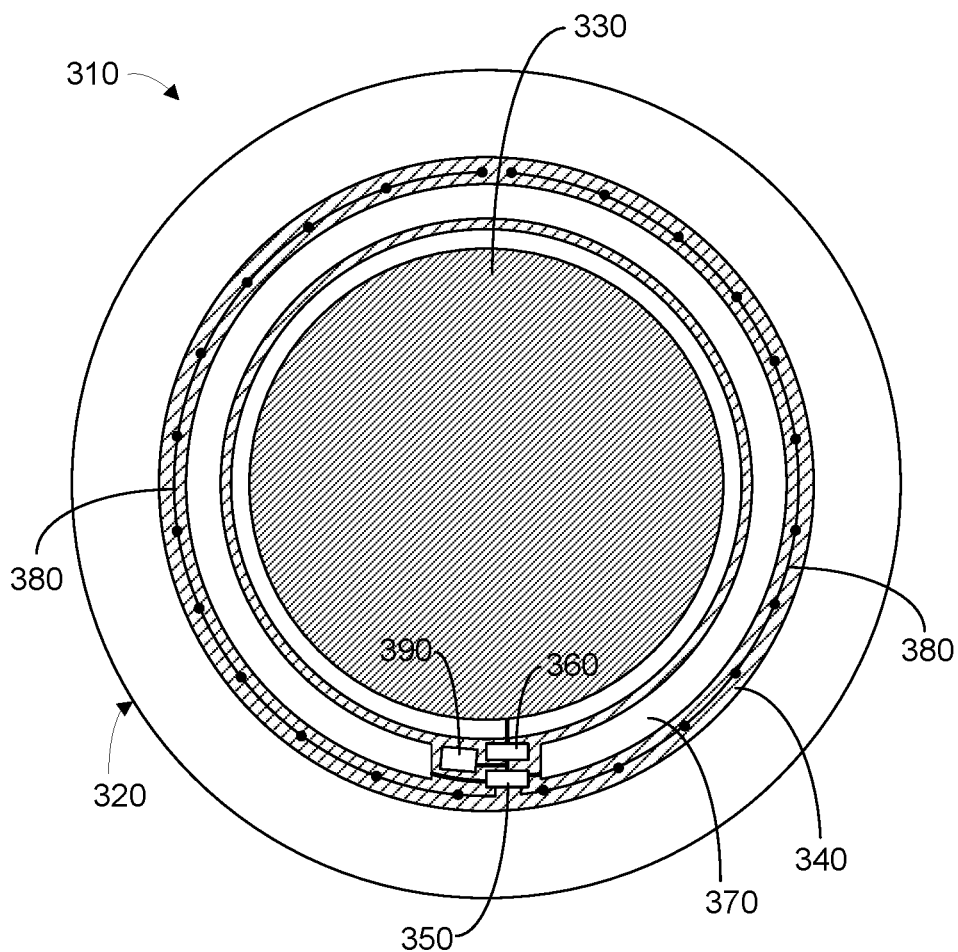
FIG. 3A is a bottom view of an example eye-mountable device.
Figure 3B:
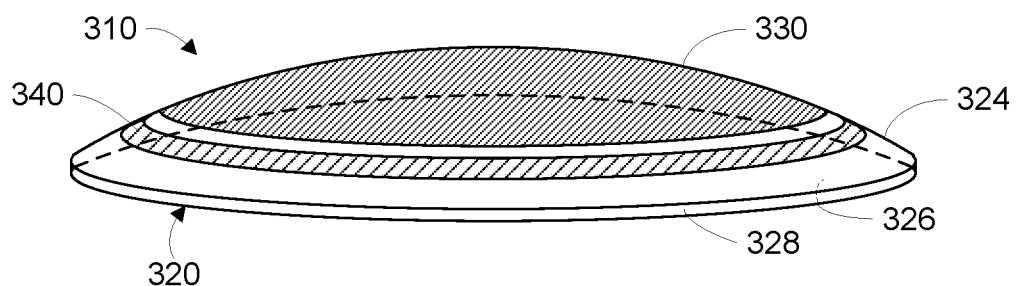
FIG. 3B is an elevational side view of the example eye-mountable device shown in FIG. 3A.

FIG. 3A is a bottom view of an example eye-mountable electronic device 310. FIG. 3B is an elevational side view of the example eye-mountable electronic device shown in FIG. 3A. It is noted that relative dimensions in FIGS. 3A and 3B are not necessarily to scale, but have been rendered for purposes of explanation only in describing the arrangement of the example eye-mountable electronic device 310. The eye-mountable device 310 is formed of a polymeric material 320 shaped as a curved disk. The polymeric material 320 can be a substantially transparent material to allow incident light to be transmitted to the eye while the eye-mountable device 310 is mounted to the eye. The polymeric material 320 can be a biocompatible material similar to those employed to form vision correction and/or cosmetic contact lenses in optometry, such as polyethylene terephthalate ("PET"), polymethyl methacrylate ("PMMA"), silicone hydrogels, rigid, gas-permeable polymeric materials, combinations of these, etc. The polymeric material 320 can be formed with one side having a concave surface 326 suitable to fit over a corneal surface of an eye. The opposing side of the disk can have a convex surface 324 that does not interfere with eyelid motion while the eye-mountable device 310 is mounted to the eye. A circular outer side edge 328 connects the concave surface 324 and convex surface 326.

The eye-mountable device 310 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 310 can be selected according to the size and/or shape of the corneal surface of the wearer's eye.

The polymeric material 320 can be formed with a curved shape in a variety of ways. For example, techniques similar to those employed to form vision-correction contact lenses, such as heat molding, injection molding, spin casting, etc. can be employed to form the polymeric material 320. While the eye-mountable device 310 is mounted in an eye, the convex surface 324 faces outward to the ambient environment while the concave surface 326 faces inward, toward the corneal surface. The convex surface 324 can therefore be considered an outer, top surface of the eye-mountable device 310 whereas the concave surface 326 can be considered an inner, bottom surface.

An electronically actuated lens 330 and a substrate 340 are embedded in the polymeric material 320. The actuated lens 330 can be similar to or the same as the electrowetting lens 200 depicted in FIGS. 2A and 2B and can be embedded in a center region of the polymeric material 320 such that incident light is transmitted through the actuated lens 330 to the eye-sensing portions of the eye. The substrate 340 can be embedded to be situated along an outer periphery of the polymeric material 320, such as partially or completely surrounding the actuated lens 330. The substrate 340 does not interfere with vision because it is too close to the eye to be in focus and is positioned away from the center region of the polymeric material 320. Moreover, the substrate 340 can be formed of a transparent material to further mitigate any effects on visual perception.

The substrate 340 can be shaped as a flat, circular ring (e.g., a disc with a central hole). The flat surface of the substrate 340 (e.g., along the radial width) can be used as a platform for mounting electronics such as chips (e.g., via flip-chip mounting) or batteries and for patterning conductive materials (e.g., via deposition techniques) to form electrodes (e.g., an anode and/or cathode of an electrochemical battery, electrodes of an electrochemical sensor), antenna (e), and/or connections. The substrate 340 and the polymeric material 320 can be approximately cylindrically symmetric about a common central axis. The substrate 340 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 340 can be implemented in a variety of different form factors.

A controller 350, a driver circuit 360, an antenna 370, a capacitive sensor system 380, and a battery 390 are disposed on the embedded substrate 340. The controller 350 can be a chip including logic elements configured to receive power from the battery 390 and to operate the driver circuit 360 to drive the actuated lens 330. The controller 350 is electrically connected to the battery 390, the capacitive sensor system 380, the antenna 370, and the driver circuit 360 by interconnects also situated on the substrate 340. The antenna 370, the interconnects, and any conductive electrodes (e.g., an anode and cathode of the battery 390) can be formed from conductive materials patterned on the substrate 340 by a process for precisely patterning such materials, such as deposition, lithography, etc. The conductive materials patterned on the substrate 340 can be, for example, gold, platinum, palladium, titanium, carbon, aluminum, copper, silver, silver-chloride, conductors formed from noble materials, metals, combinations of these, etc.

As shown in FIG. 3A, which is a view facing the concave surface 326 of the eye-mountable device 310, the battery 390, capacitive sensor system 380, antenna 370, driver circuit 360, and controller 350 are mounted to a side of the substrate 340 facing the concave surface 326. However, these electronics can be mounted to either the "inward" facing side (e.g., situated closest to the concave surface 326) or the "outward" facing side (e.g., situated closest to the convex surface 324) of the substrate 340. Moreover, in some embodiments, some electronic components can be mounted on one side of the substrate 340, while other electronic components are mounted to the opposing side, and connections between the two can be made via conductive materials passing through the substrate 340.

As shown, the antenna 370 can take the form of a loop antenna. Such a loop antenna can be a layer of conductive material patterned along the flat surface of the substrate 340 to form a flat conductive ring. In some instances, such a loop antenna can be formed without making a complete loop. For instance, such an antenna can have a cutout to allow room for the controller 350 or other elements of the device 310. However, such a loop antenna can also be arranged as a continuous strip of conductive material that wraps entirely around the flat surface of the substrate 340 one or more times. For example, a strip of conductive material with multiple windings can be patterned on the side of the substrate 340 opposite the controller 350, driver circuit 360, and battery 390. Interconnects between the ends of such a wound antenna (e.g., the antenna leads) can be passed through the substrate 340 to the controller 350. Such a loop antenna could be used to facilitate additional functionality, e.g., to provide means for communicating with other devices (e.g., with an implanted device that is receiving wireless power from the eye-mountable device 310 via the loop antenna and/or via some other means), to provide means for recharging a rechargeable battery of the eye-mountable device 310 (e.g., battery 390), or to provide some other functionality.

The capacitive sensor system 380 can be arranged on the substrate 340 to sense eyelid overlap in a manner similar to capacitive touch screens. By monitoring the amount and position of eyelid overlap, feedback signals from the capacitive sensor system 380 may be measured by the controller 350 to determine the approximate gaze direction and/or focal distance of the eye. The controller 350 may then use the determined gaze direction and/or focal distance of the eye to control an optical power provided to the eye. For instance, based on the measured gaze direction and/or focal distance, the controller 350 may adjust a voltage or current that the driver circuit 360 provides to the actuated lens 330. In the illustrated embodiment, the capacitive sensor system 380 is distributed peripherally around the antenna 370 along an outer edge of the substrate 340. In other embodiments, the capacitive sensor system 380 may be distributed in alternative manners in or on the eye-mountable device 310. In the illustrated embodiment, the capacitive sensor system 380 includes a number of discrete capacitance sensors coupled to a common read-line; however, various implementations include a single elongated capacitance sensor, a number of discrete capacitance sensors, multiple discrete capacitance sensors coupled in parallel via a common read-line, multiple independent branches of parallel coupled discrete capacitance sensors, etc. In another embodiment, photodetectors may be variously disposed on or in the eye-mountable device 310 to provide for monitoring of viewing actions based on light levels (e.g., including changes in such levels, etc.) rather than, or in addition to, capacitive sensing.

Further, note that the configuration of the battery 390 is intended as a non-limiting example. The eye-mountable device 310 could include multiple discrete batteries that could be electrically connected in series, in parallel, or according to some other consideration. One or more elements of the battery 390 (e.g., an anode, a cathode) could be formed as conductive traces patterned on the substrate 340. Additionally or alternatively, the battery 390 could be formed independently of the substrate 340 and subsequently disposed on the substrate 340 (e.g., using solder, using an adhesive, by potting the battery 390 and substrate 340 proximate each other in a precursor material used to form the polymeric material 320). The battery 390 could be rechargeable (e.g., could have a lithium-polymer chemistry) or could be non-rechargeable. In some examples, the battery 390 could be activated by exposure to tears or some other aqueous fluid of an eye (e.g., the battery 390 could be a zinc battery that is activated by exposure to an aqueous fluid in which oxygen is dissolved).

Figure 3C:
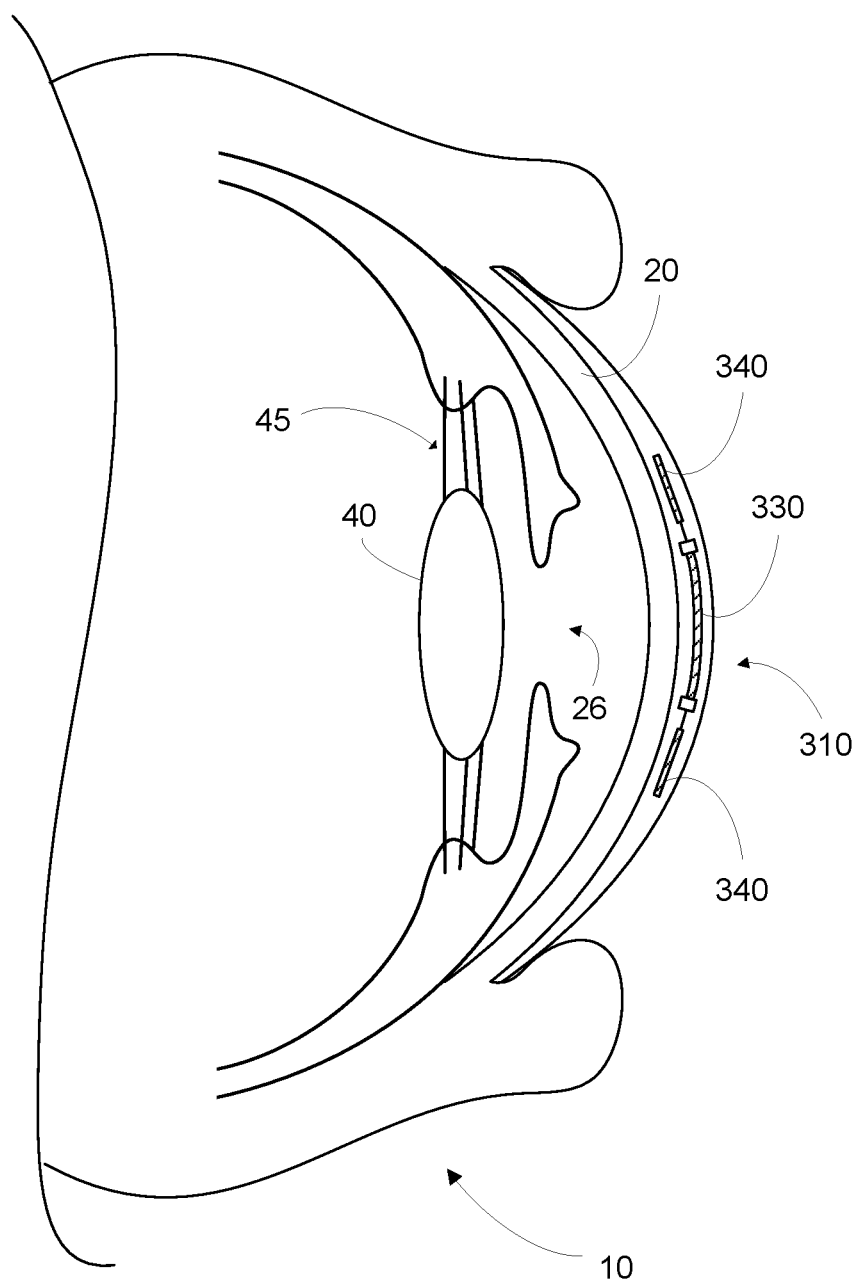
FIG. 3C is a side cross-section view of the example eye-mountable device shown in FIGS. 3A and 3B while mounted to a corneal surface of an eye.

FIG. 3C is a side cross-section view of the example eye-mountable device 310 while mounted to the corneal surface 20 of the eye 10 shown in FIG. 1C. As shown in the cross-sectional view in FIG. 3C, the substrate 340 can be inclined such that the flat mounting surfaces of the substrate 340 are approximately parallel to the adjacent portion of the concave surface 326. As described above, the substrate 340 is a flattened ring with an inward-facing surface (closer to the concave surface 326 of the polymeric material 320) and an outward-facing surface (closer to the convex surface 324), and the substrate 340 can have electronic components and/or patterned conductive materials mounted to either or both mounting surfaces.

As further shown in the cross-sectional view in FIG. 3C, the eye-mountable device 310 may be positioned on the corneal surface 20 such that the actuated lens 330 substantially aligns with the pupil 26 of the eye 10. In this manner, light that passes through the pupil 26 to the lens 40 of the eye 10 can first pass through the actuated lens 330 of the eye-mountable device 310. In line with the discussion above, the actuated lens 330 could take various forms and could be similar to or the same as the electrowetting lens 200 shown in FIGS. 2A and 2B.

As further shown, the actuated lens 330 can be mechanically coupled to the substrate 340 and electrically coupled by one or more interconnects to various other components of the eye-mountable device 310, such as the controller 350. Thus, in line with the discussion above, the controller 350 can operate the actuated lens 330 to adjust an optical power of the actuated lens 330 (and therefore an overall optical power provided to the eye 10) by applying a voltage, current, or other electrical signal to the electronically actuated lens.

The eye-mountable device 310 could further include elements related to an application of the eye-mountable device 310 to detect accommodation forces generated by an eye (e.g., accommodation forces that are applied to the lens capsule 40 of the eye 10 by zonules 45 of the eye 10) and to provide a controllable optical power to the eye 10 related to the detected accommodation forces. These elements could include accommodation sensors configured to detect the accommodation forces. Such accommodation sensors could include sensors or sensor interfaces implanted within the lens capsule and/or sensors located on the eye-mountable device 310 and configured to detect haptics of the eye-mountable device 310 itself. As such, the eye-mountable device 310 could further include one or more transmitters and/or receivers configured to communicate with the accommodation sensors (e.g., by emitting and/or receiving light, radio frequency electromagnetic fields, or other wireless transmissions) to receive information from the accommodation sensors indicative of the detected accommodation forces. The controller 350 of the eye-mountable device 310 could thus be configured to adjust a voltage or current provided to the actuated lens 330 to provide a controllable optical power to the eye 10 based on the detected accommodation forces.

The eye-mountable device 310 could further include one or more sensors (not shown) configured to detect physiological parameters of a body (e.g., concentrations of analytes in tears or other bodily fluids, an amount of blood in a portion of subsurface vasculature of the sclera or eyelid, an oxygenation state of blood, or whether an eyelid is closed), properties of the environment of the device (e.g., an ambient illumination, a barometric pressure, or a temperature), properties of the device (e.g., an acceleration or an orientation), or to detect some other information. Such sensors could include accelerometers, electrodes (e.g., electrodes of an electrochemical analyte sensor, electrodes of an electrophysiological sensor configured to detect an electrocardiogram, an electrooculogram, an electromyogram, or some other bioelectrical signal), light detectors, thermometers, gyroscopes, capacitance sensors, pressure sensors, strain gauges, light emitters, microphones, or other elements configured to detect one or more physical variables related to a property of interest. The eye-mountable devices as shown herein could operate such elements to measure physiological parameters or other information of interest at one or more points in time. Such measured properties and/or parameters could be recorded (e.g., in a memory of the device, for example, for later transmission to an external system), transmitted to an external system, indicated using elements of the device (e.g., using a display, using one or more light-emitting elements), used to determine a health state of a user, or used according to some other application.

As noted above, a battery of the eye-mountable device 310 could be single use (i.e., non-rechargeable) or could be rechargeable. In examples where the battery is rechargeable, the eye-mountable device could be configured in a variety of ways to facilitate reception of energy to recharge the battery. The eye-mountable device 310 could include an antenna (e.g., a loop antenna) to receive radio frequency electromagnetic energy, a photovoltaic cell or other light receiving element(s) to receive optical energy, two or more electrodes to receive electrical currents (e.g., via direct contact with corresponding electrodes of a recharger and/or via a conductive fluid in which the eye-mountable device is disposed), or some other means for receiving energy from an external device. For example, a loop antenna could be used to receive radio frequency electromagnetic energy to recharge the battery.

IV. Example Electronics of Devices

Figure 4:
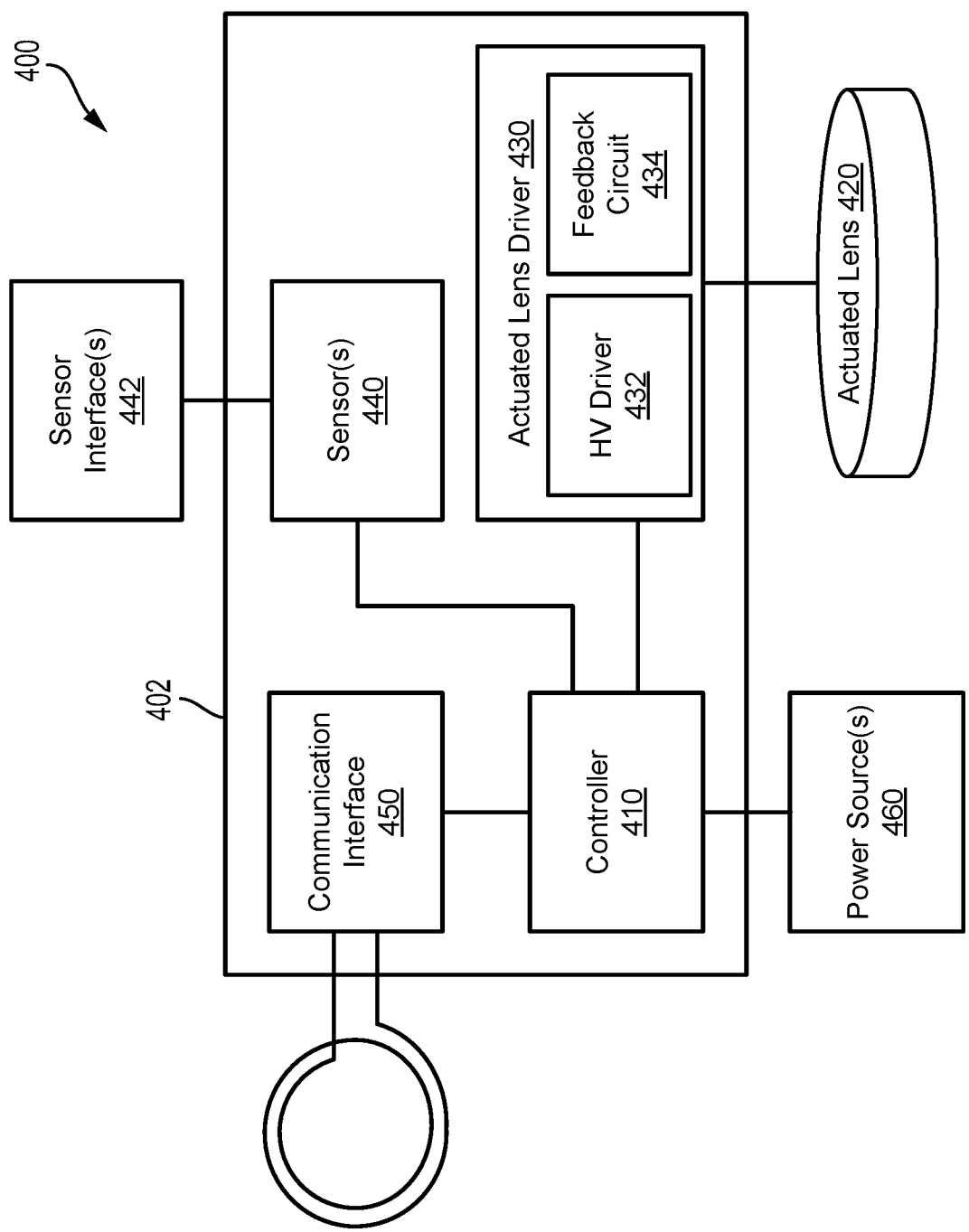
FIG. 4 is a block diagram of an example eye-implantable and/or eye-mountable system.

FIG. 4 is a block diagram of a system 400 that could be implemented as part of an eye-implantable device such as the eye-implantable device 100 depicted in FIG. 1A, an extraocular device (e.g., an eye-mountable device such as the eye-mountable device 310 depicted in FIGS. 3A-3C, a head-mountable device, some other type of body-mountable device, a smart phone, etc.), or a combination of the two. The system 400 includes various electronic components arranged as part of and/or configured to interface with an integrated circuit 402. In particular, the system 400 includes a controller 410, an actuated lens 420, an actuated lens driver 430, one or more sensor(s) 440, one or more sensor interface(s) 442, a communication interface 450, and one or more power source(s) 460, such as a battery (e.g., single-use alkaline batteries, rechargeable lithium-polymer batteries), a solar cell, or some other source of energy for powering the controller 410 or other elements of the system 400.

As shown, the controller 410, actuated lens driver 430, sensor(s) 440, and communication interface 450 are included in the integrated circuit 402. However, this is meant as a non-limiting example, and in other embodiments, additional or fewer elements of the system 400 can be included in the integrated circuit 402. The integrated circuit 402 may be arranged on a substrate, and the substrate can take various forms. For instance, in embodiments where the system 400 is an eye-implantable device, the substrate can be similar to the substrate 108 of the eye-implantable device 100 depicted in FIG. 1A, and in embodiments where the system The actuated lens driver 430 is operable to control an optical power that is provided to the eye by the actuated lens 420. The actuated lens 420 may include an electrowetting lens, such as the electrowetting lens 200 shown in FIGS. 2A and 2B, and operating the actuated lens 420 to control the optical power of the lens could include applying a voltage to electrodes of the electrowetting actuated lens. This could involve applying a voltage to the lens that is larger in magnitude than a voltage that is supplied to the controller 410 or other components of the system 400. As such, in order to control the optical power of the electrowetting lens, the actuated lens driver 430 may include a high voltage (HV) driver 432 for providing higher voltages (e.g., voltages greater than ±20V). The HV driver 432 could include charge pumps, voltage multipliers, or various other types of voltage converters to provide such higher voltages. As further shown, the actuated lens driver 430 may include a feedback circuit 434 for controlling the output voltage of the HV driver 432 and thus controlling the optical power provided to the eye by the actuated lens 420. Examples of the HV driver 432 and the feedback circuit 434 are shown in more detail below with respect to FIGS. 5A-9.

The sensor(s) 440 may include sensors configured to detect physiological properties (e.g., a pupillary diameter of an eye, a pressure or force, or a biopotential), environmental parameters (e.g., an ambient light level, a distance between eyes of a user and an object at which the user is looking), to detect movements of the eye and/or eyelids of a user (e.g., to detect a vergence of the eyes), or to otherwise detect physical parameters that may be relevant to the operation of an extraocular device and/or an eye-implantable device. In a particular example, the sensor(s) 440 could include an accommodation sensor of an eye-implantable device configured to detect, directly or indirectly, accommodation forces exerted on a lens capsule of the eye, e.g., by detecting a force or pressure within the lens capsule via sensor interface(s) 442, which may include an elastic material disposed in the lens capsule, an interface for detecting electrical activity of the ciliary muscles, or some other means. In line with the discussion above, a particular example of an accommodation sensor can include a capacitive sensor system (e.g., the capacitive sensor system 380 in FIG. 3A) for sensing an amount and position of eyelid overlap.

The communication interface 450 can be operated to wirelessly transmit sensor data, commands, power, or other signals between an eye-implantable device and an extraocular device or between two or more extraocular devices. For instance, the eye-implantable device and/or the extraocular device can include light-emitting elements (e.g., LEDs, lasers, VC SELs), radio-frequency electromagnetic energy-transmitting elements (e.g., antennas, coils), elements configured to inject a time-varying current into tissues or fluids of the body (e.g., electrodes), or other elements configured to transmit. The communication interface 450 could be configured to control an intensity, a phase, a frequency, a polarization, a direction, or some other properties of wireless signals transmitted from the communication interface 450 to indicate information.

An eye-implantable device and/or an extraocular device of the system 400 could include additional or alternative elements, and could include more or fewer elements than those illustrated in FIG. 4. For instance, the eye-implantable device could include elements configured to transmit wireless signals to the extraocular device, and the extraocular device could include elements configure to receive such transmitted signals. In such an example, the eye-implanted device and the extraocular device could additionally include a transmitter and receiver, respectively. Additionally or alternatively, the illustrated communication interface 450 could be configured as one or more transceivers to facilitate bidirectional communication and/or to share one or more elements (e.g., antennas, filters, coils, power conditioning systems) in common with other elements configured to facilitate bidirectional communication.

It is noted that the block diagram shown in FIG. 4 is described in connection with functional modules for convenience in description. However, embodiments of the system 400 can include an extraocular device and/or an eye-implanted device arranged with one or more of the functional modules ("sub-systems") implemented in a single chip, integrated circuit, and/or physical feature. That is, the functional blocks in FIG. 4 need not be implemented as separated modules. Moreover, one or more of the functional modules described in FIG. 4 can be implemented by separately packaged chips or other components electrically connected to one another. Further, note that an extraocular device and/or an eye-implantable device as described herein could include additional or alternative components to those shown in FIG. 4 (e.g., additional sensors, actuated lenses, displays, retinal stimulator arrays, electrodes, batteries, controllers, transmitters, receivers, stimulators, etc.).

Figure 5A:
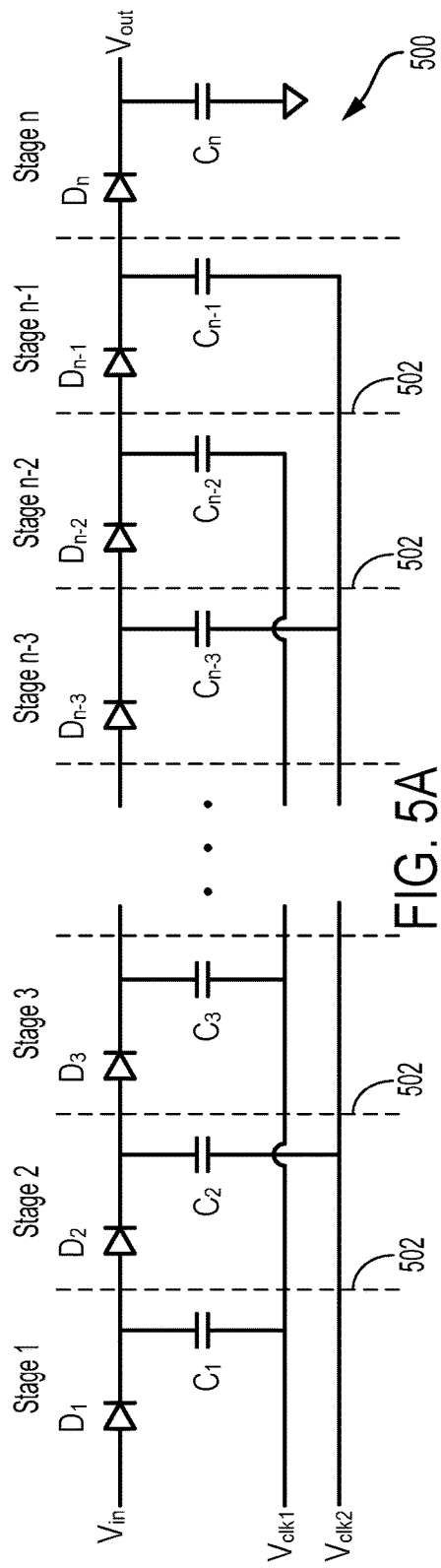
FIG. 5A is a simplified circuit diagram of a charge pump that can be used to charge an electrowetting lens.

FIG. 5A is a circuit diagram of a charge pump 500 that can be used to pump charge (e.g., provide a positive voltage) to an electrowetting lens. The charge pump 500 as shown is a Dickson charge pump, but it should be understood that the charge pump 500 can take various other forms, such as a Cockcroft-Walton voltage multiplier, a Greinacher voltage multiplier, or the like. The charge pump 500 is operable to receive a DC input voltage $V_{in}$ and output a DC output voltage $V_{out}$, with $V_{out}$ being greater in magnitude than $V_{in}$. As shown, the charge pump 500 includes a number of stages separated by dashed lines 502, and each stage includes a diode and a capacitor. For instance, the first stage includes a first diode $D_1$ and a first capacitor $C_1$ coupled to the cathode of the first diode $D_1$, the second stage includes a second diode $D_2$ and a second capacitor $C_2$ coupled to the cathode of the second diode $D_2$, and so on, up to the nth stage. Each stage has its input at the anode of its diode and its output at the cathode of its diode. For instance, the input of the first stage is at the anode of the first diode $D_1$, and the output of the first stage is at the cathode of the first diode $D_1$.

As further shown, each stage of the charge pump 500 is coupled to a reference voltage signal $V_{clk1}$ or $V_{clk2}$. Odd numbered stages are coupled to $V_{clk1}$ and even numbered stages are coupled to $V_{clk2}$. FIG. 5C is a timing diagram of the reference voltage signals $V_{clk1}$ and $V_{clk2}$ that can be used in connection with the charge pump 500. As shown in FIG. 5C, $V_{clk1}$ and $V_{clk2}$ can be clock pulse signals that are in antiphase with one another, such that $V_{clk1}$ is low when $V_{clk2}$ is high and $V_{clk1}$ is high when $V_{clk2}$ is low. Further, the reference voltage signals $V_{clk1}$ and $V_{clk2}$ can alternate between a voltage level of 0V and $V_{in}$.

In some examples, the reference voltage signals $V_{clk1}$ and $V_{clk2}$ can be generated using an oscillator or a digital clock signal. However, a typical oscillator or digital clock may not be capable of outputting enough current to drive the charge pump 500. As such, a level converter circuit can be used to generate the reference voltage signals $V_{clk1}$ and $V_{clk2}$ based on a low power oscillator or digital clock signal.

Figure 6A:
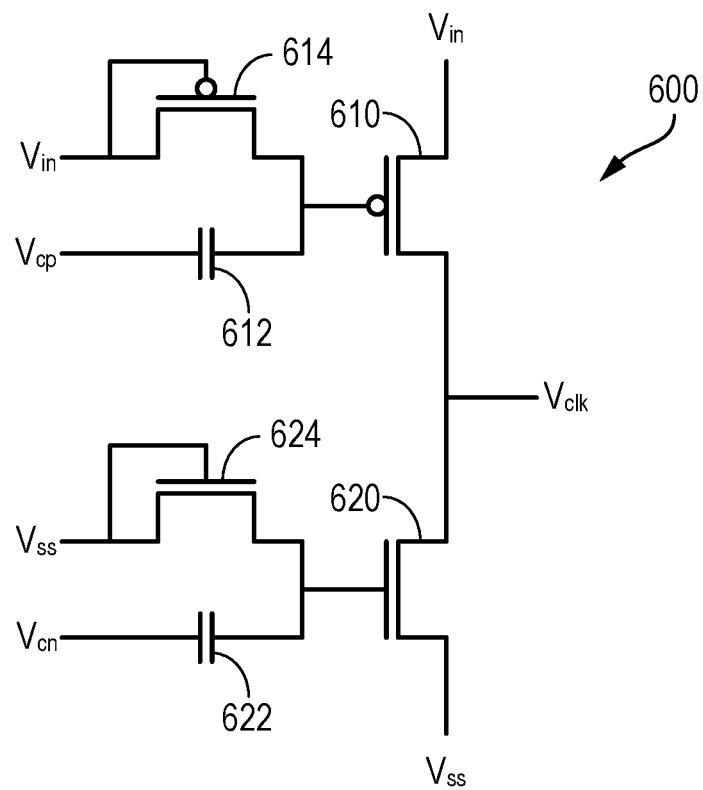
FIG. 6A is a simplified circuit diagram of a level converter that can be used to generate the signals shown in FIG. 5C.

FIG. 6A is a circuit diagram of a level converter 600 that can be used to generate the reference voltage signals $V_{clk1}$ and $V_{clk2}$. As shown, the level converter 600 includes a pMOS transistor 610 and an nMOS transistor 620 connected in a complementary metal-oxide-semiconductor (CMOS) configuration between voltage rails of $V_{in}$ at the source terminal of the pMOS transistor 610 and $V_{ss}$ (e.g., 0V) at the source terminal of the nMOS transistor 620.

The output $V_{clk}$ of the level converter 600 is coupled to the drain terminals of the pMOS transistor 610 and nMOS transistor 620. As such, when the pMOS transistor 610 is on and the nMOS transistor 620 is off, the output $V_{clk}$ is pulled up to $V_{in}$. Similarly, when the pMOS transistor 610 is off and the nMOS transistor 620 is on, the output $V_{clk}$ is pulled down to $V_{ss}$. Thus, by turning on the pMOS transistor 610 and the nMOS transistor 620 in an alternating pattern, the output $V_{clk}$ (can alternate between $V_{in}$ and 0V as shown in FIG. 5C. And by operating two of the level converters 600 in anti-phase with one another, the outputs of the level converters 600 can be used as the reference voltages $V_{clk1}$ and $V_{clk2}$ as shown in FIG. 5A.

In order to run on the pMOS transistor 610 and the nMOS transistor 620 in an alternating pattern, a first clock signal $V_{cp}$ can be coupled to the gate terminal of the pMOS transistor 610 through a first filter capacitor 612, and a second clock signal $V_{cn}$ can be applied to the gate terminal of the nMOS transistor 620 through a second filter capacitor 622.

Figure 6B:
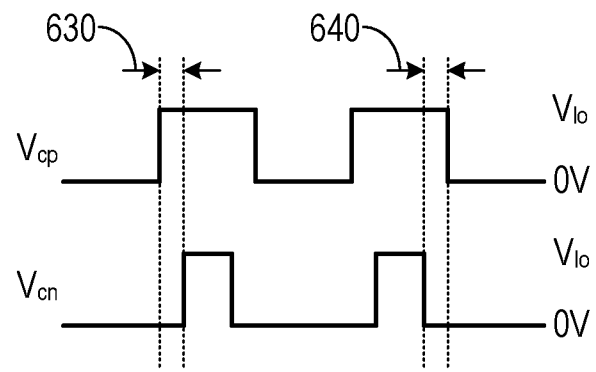
FIG. 6B is a timing diagram of voltage signals that can be provided to the level converter shown in FIG. 6A.

FIG. 6B is a timing diagram of the clock signals $V_{cp}$ and $V_{cn}$ that can be coupled to the gate terminals of the pMOS transistor 610 and nMOS transistor 620 of the level converter 600. As shown, the clock signals $V_{cp}$ and $V_{cn}$ can transition between 0V and a logic high voltage level $V_{lo}$, and these clock signals are applied to the gate terminals of the pMOS and nMOS transistors 610, 620. The level converter 600 can further include a diode-connected pMOS transistor 614 coupled to the gate terminal of the pMOS transistor 610, as well as a diode-connected nMOS transistor 624 coupled to the gate terminal of the nMOS transistor 620. These diode-connected transistors 614, 624 can act as non-linear resistors so that when $V_{cp}$ transitions to $V_{lo}$, the voltage at the gate terminal of the pMOS transistor 610 is set to $V_{in}$, and when $V_{cn}$ transitions to 0V, the voltage at the gate terminal of the nMOS transistor 620 is set to $V_{ss}$.

Further, the clock signals $V_{cp}$ and $V_{cn}$ can be configured to transition in phase with one another in order to turn on the pMOS transistor 610 and the nMOS transistor 620 in an alternating pattern. When the gate voltages of both the pMOS transistor 610 and the nMOS transistor 620 are high, the pMOS transistor 610 is off and the nMOS transistor is on. When the gate voltages of both the pMOS transistor 610 and the nMOS transistor 620 are low, the pMOS transistor 610 is on and the nMOS transistor is off. Thus, by configuring the clock signals $V_{cp}$ and $V_{cn}$ to be in phase with one another, the pMOS transistor 610 and the nMOS transistor 620 can be turned on in an alternating pattern.

As further shown in FIG. 6B, the clock signals $V_{cp}$ and $V_{cn}$ can have different duty cycles. This can reduce or eliminate shoot-through current by using "break-before-make" switching in order to avoid a situation where both the pMOS transistor 610 and the nMOS transistor 620 are on at the same time. If both the pMOS transistor 610 and the nMOS transistor 620 are on at the same time, then the transistors 610, 620 effectively form a short circuit path between $V_{in}$ and $V_{ss}$, thereby wasting power and lowering efficiency of the level converter 600. This can be particularly problematic when the system is powered using a battery or some other limited energy source, as is the case with the eye-implantable and eye-mountable systems described above. Thus, as shown in FIG. 6B, the clock signal $V_{cn}$ can be configured to have its rising edge transition (e.g., its transition from 0V to $V_{lo}$) occur at a time delay 630 after the clock signal $V_{cp}$ has its rising edge transition. Similarly, the clock signal $V_{cn}$ can be further configured to have its falling edge transition (e.g., its transition from $V_{lo}$ to 0V) occur at a time delay 640 after the clock signal $V_{cp}$ has its falling edge transition. In this manner, $V_{cn}$ will not be logic high when $V_{cp}$ is logic low, such that the nMOS transistor 620 will not be turned on until after the pMOS transistor 610 is turned off and the pMOS transistor 610 will not be turned on until after the nMOS transistor 620 is turned off.

Figure 7:
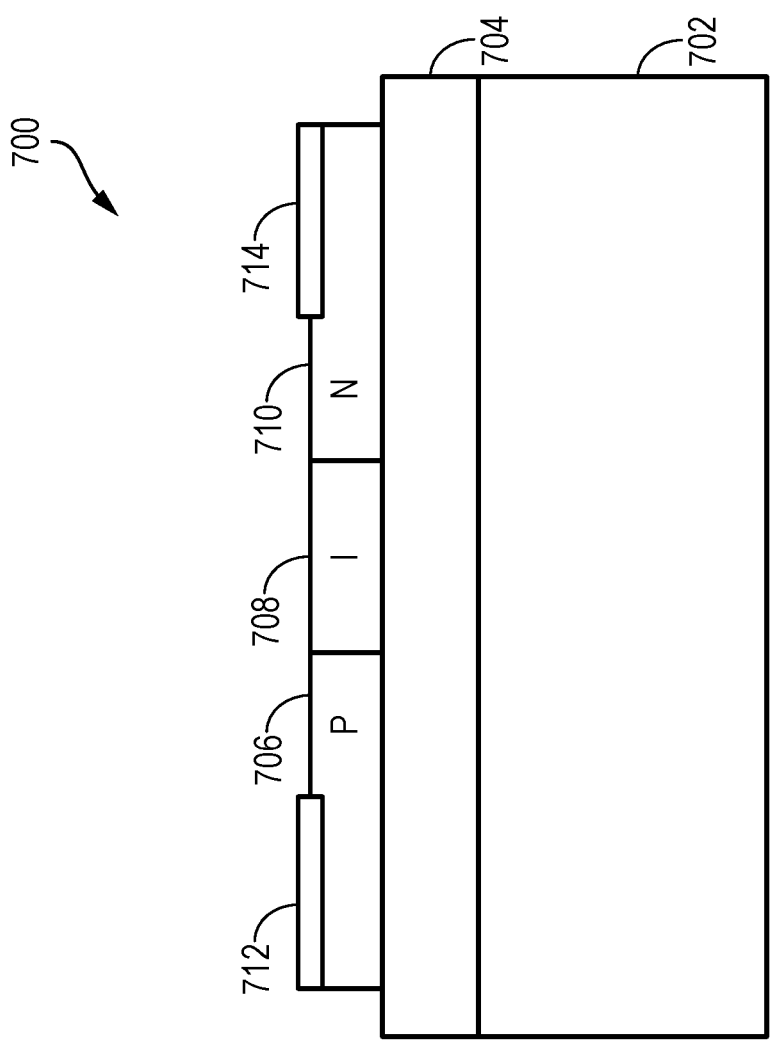
FIG. 7 is a simplified diagram of a PIN diode that can be used in the charge pumps shown in FIGS. 5A and 5B.

In some examples, in order to further reduce the power consumption and improve the efficiency of the system, the diodes $D_1$-$D_n$ of the charge pump 500 can be above-substrate PIN diodes, which can have lower reverse-bias current leakage than traditional well-based PN diodes. FIG. 7 is a simplified diagram of an example PIN diode 700. The diode 700 includes a semiconductor substrate 702 (e.g., a silicon substrate) and a shallow trench isolation (STI) layer 704 on top of the substrate 702. The STI layer 704 can include one or more dielectric materials (e.g., silicon dioxide) that electrically insulate electronics located above the STI layer 704 from the substrate 702.

The diode 700 further includes on top of the STI layer 704 a PIN junction formed from a p-doped region 706, an n-doped region 710, and an undoped intrinsic region 708 between the p-doped region 706 and the n-doped region 710. An anode contact 712 can be formed (e.g., from p-type polycrystalline silicon) on the p-doped region 706, and a cathode contact 714 can be formed (e.g., from n-type polycrystalline silicon) on the n-doped region 710. It is noted that relative dimensions in FIG. 7 are not necessarily to scale, but have been rendered for purposes of explanation only in describing the arrangement of the example PIN diode 700.

Referring back to FIG. 5A, when the charge pump 500 is in operation and reaches steady state, the first capacitor $C_1$ in the first stage will be charged with a voltage approximately equal to $V_{in}$. The output of the first stage is equal to the sum of the reference voltage $V_{clk1}$ and the voltage across the first capacitor $C_1$ such that, when the reference voltage $V_{clk1}$ transitions from 0V to $V_{in}$, the output of the first stage, and consequently the input to the second stage, is equal to approximately twice the voltage of $V_{in}$. As such, in steady state, the second capacitor $C_2$ in the second stage will be charged with a voltage approximately equal to 2V And when the reference voltage $V_{clk2}$ of the second stage transitions from 0V to $V_{in}$, the output of the second stage and the input to the third stage is equal to approximately three times the voltage of Each subsequent stage of the charge pump acts in a similar manner. Thus, each stage of the charge pump 500 increases the output voltage by the voltage of $V_{in}$, except for the nth stage, which acts as a voltage rectifier to produce a DC output at $V_{out}$. The output $V_{out}$ of the charge pump 500 can thus be varied by adjusting the number of stages and/or by adjusting the magnitude of $V_{in}$.

Further, it should be understood that the example charge pump 500 is described above in ideal conditions, and the actual voltage across each capacitor $C_1$-$C_n$ may be slightly lower due to voltage drops across the diodes $D_1$-$D_n$ and/or other sources of losses in the circuit.

In practice, the charge pump 500 can be coupled to an electrowetting lens of an eye-implanted or eye-mountable device in order to apply the output voltage $V_{out}$ across the electrodes of the electrowetting lens. In this manner, adjusting the output voltage $V_{out}$ can adjust the voltage across the electrodes of the electrowetting lens and can thus adjust an optical power of the electrowetting lens as discussed above.

As further noted above, the electrowetting lens can have capacitive characteristics, such that the electrodes of the electrowetting lens may tend to hold charge and resist any changes in voltage across the electrodes. For instance, if the charge pump 500 is coupled to the electrodes of the electrowetting lens and charges the electrodes to a particular voltage and if the charge pump 500 is then decoupled from the electrowetting lens, the electrowetting lens may tend to stay at the charged voltage or slowly discharge. However, in order to rapidly change an optical power of the electrowetting lens, it may be desirable to configure the electrowetting lens to rapidly discharge. In accordance with the present disclosure, this can be achieved by coupling a second charge pump to the electrodes of the electrowetting lens that is configured to actively pump charge away from the lens.

Figure 5B:
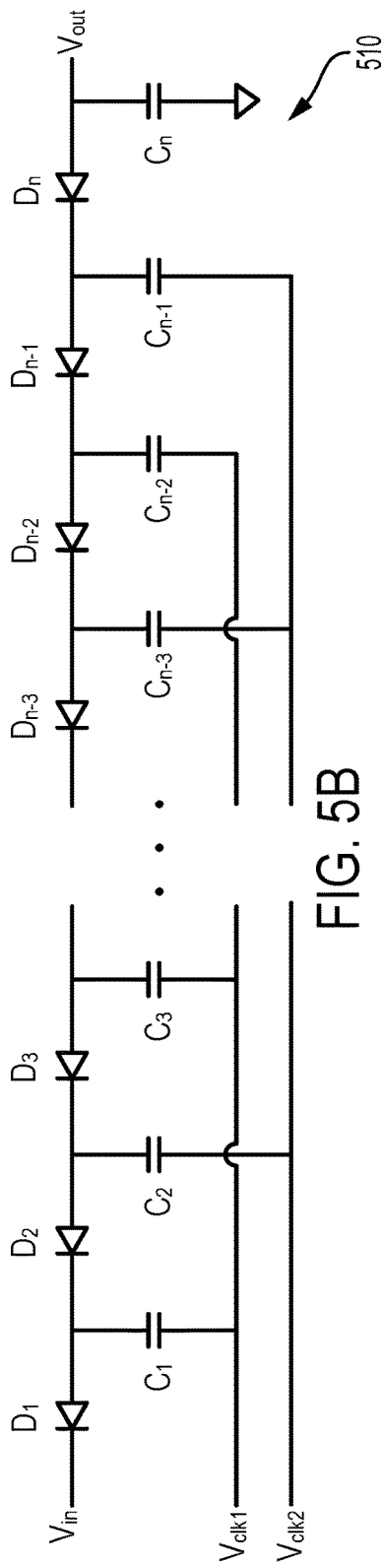
FIG. 5B is a simplified circuit diagram of a charge pump that can be used to discharge an electrowetting lens.
Figure 5C:
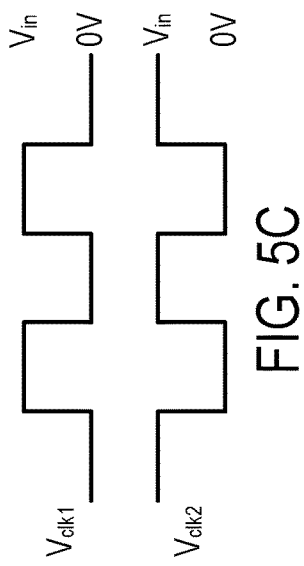
FIG. 5C is a timing diagram of voltage signals that can be provided to the charge pumps shown in FIGS. 5A and 5B.

FIG. 5B is a circuit diagram of a charge pump 510 that can be used to pump charge away from (e.g., provide a negative voltage to) an electrowetting lens. As shown, the charge pump 510 in FIG. 5B is arranged in a similar manner as the charge pump 500 in FIG. 5A, except the diodes $D_1$-$D_n$ are reversed in polarity such that the input of each stage is at the cathode of each diode and the output of each stage is at the anode of each diode. In this manner, rather than multiplying $V_{in}$ to generate a positive voltage at $V_{out}$, the charge pump 510 is configured to multiply $V_{in}$ to generate a negative voltage at $V_{out}$. Thus, in practice, the charge pump 500 in FIG. 5A can be coupled to the electrowetting lens to charge the electrowetting lens, and, to discharge the electrowetting lens, the charge pump 500 can be decoupled from the electrowetting lens and the charge pump 510 in FIG. 5B can be coupled to the electrowetting lens instead.

As another example, both the charge pump 500 in FIG. 5A and the charge pump 510 in FIG. 5B can be coupled to the electrowetting lens concurrently, and the charge pumps 500, 510 can be operated such that only one of the charge pumps 500, 510 is active at a given time. For instance, in order to pump charge to the electrowetting lens, charge pump 500 can be turned on (e.g., by applying the clock signals in FIG. 5C to the $V_{clk1}$ and $V_{clk2}$ inputs in FIG. 5A) and charge pump 510 can be turned off (e.g., by tying the $V_{clk1}$ and $V_{clk2}$ inputs in FIG. 5B to a ground voltage). Similarly, in order to pump charge away from the electrowetting lens, charge pump 510 can be turned on (e.g., by applying the clock signals in FIG. 5C to the $V_{clk1}$ and $V_{clk2}$ inputs in FIG. 5B) and charge pump 500 can be turned off (e.g., by tying the $V_{clk1}$ and $V_{clk2}$ inputs in FIG. 5A to a ground voltage). Further, in this example, because the outputs of the charge pumps 500, 510 are electrically connected, the voltage difference between the output voltage $V_{out}$ of charge pump 500 and the input voltage $V_{in}$ of charge pump 510 is accounted for by a series of voltage drops across each of the diodes $D_{1-n}$ of charge pump 510. As such, in order to minimize power loss due to diode current through the diodes $D_{1-n}$ of charge pump 510, charge pump 510 could include a sufficient number of stages such that the voltage drops across each of the diodes $D_{1-n}$ are reduced below the forward bias threshold voltage of the diodes $D_{1-n}$.

While the above examples describe charging the electrowetting lens using the charge pump 500 in FIG. 5A and discharging the electrowetting lens using the charge pump 510 in FIG. 5B, the reverse process is also possible. For instance, the charge pump 510 in FIG. 5B can be coupled to the electrowetting lens to charge the electrowetting lens with negative charge, and the charge pump 500 in FIG. 5A can then be coupled to the electrowetting lens to discharge the electrowetting lens.

In some examples, an eye-implantable device or eye-mountable device may include a system for monitoring and controlling the voltage that is supplied to the electrowetting lens. For example, the device could include a resistive voltage divider for stepping down the output voltage $V_{out}$ of the charge pumps 500, 510 shown in FIGS. 5A and 5B to a lower voltage that is measurable by a digital circuit. However, resistive voltage dividers can add unwanted power losses to the device due to power dissipation in the resistors. And, as noted above, it may be desirable to reduce or eliminate as many power losses in an eye-implantable device or eye-mountable device in order to increase battery life of the device. Thus, in accordance with the present disclosure, the eye-implantable or eye-mountable device can include a voltage-sensing circuit for reducing power losses in the device.

Figure 8:
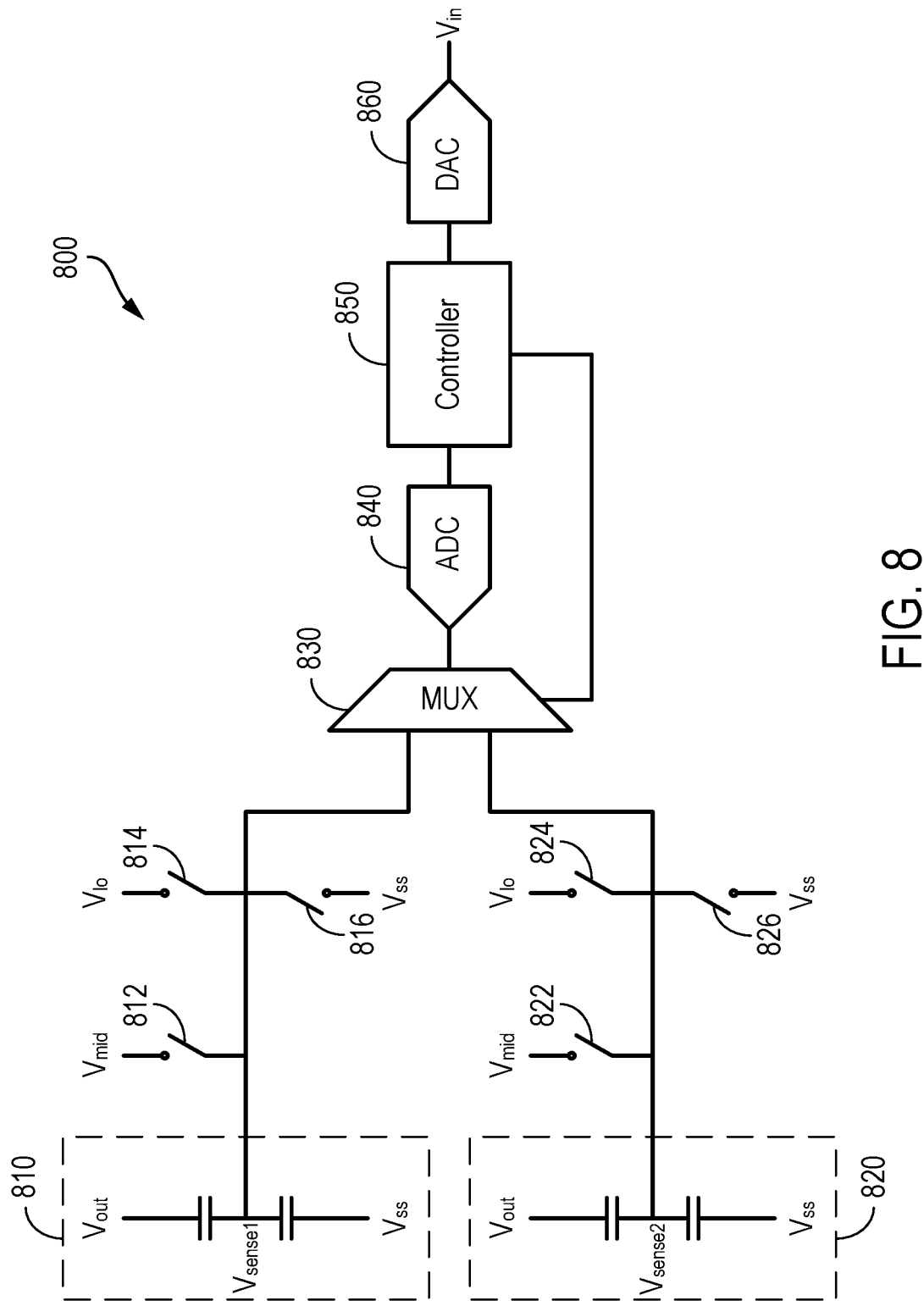
FIG. 8 is a simplified diagram of a voltage-sensing circuit for monitoring and controlling the output voltage of the charge pumps shown in FIGS. 5A and 5B.

FIG. 8 is a simplified diagram of such a voltage-sensing circuit 800 for monitoring and controlling the output voltage $V_{out}$ of the charge pumps 500, 510 shown in FIGS. 5A and 5B. The voltage-sensing circuit 800 includes a first capacitive voltage divider 810 having a first voltage output $V_{sense1}$, a second capacitive voltage divider 820 having a second voltage output $V_{sense2}$, a multiplexer 830, an analog-to-digital converter (ADC) 840, a controller 850, and a digital-to-analog converter (DAC) 860.

In practice, the voltage-sensing circuit 800 can be used to monitor the voltage $V_{out}$ applied to the electrowetting lens whenever the electrowetting lens transitions from being coupled to one of the charge pumps 500, 510 to being coupled to the other. For instance, the voltage-sensing circuit 800 can monitor $V_{out}$ when the device decouples charge pump 500 from the electrowetting lens and couples charge pump 510 to the electrowetting lens or when the device decouples charge pump 510 from the electrowetting lens and couples charge pump 500 to the electrowetting lens.

In an example process, when such a charge pump transition occurs, the output $V_{sense1}$ of the first capacitive voltage divider 810 can be reset to $V_{lo}$ or $V_{ss}$ using reset switch 814 or reset switch 816, depending on whether the transition is from charge pump 500 to charge pump 510 or from charge pump 510 to charge pump 500. For instance, if the electrowetting lens transitions from being coupled to charge pump 500 to being coupled to charge pump 510, then reset switch 814 can be closed to set the voltage of $V_{sense1}$ to be $V_{lo}$, and the reset switch 814 can then be reopened to allow $V_{sense1}$ to drift downwards as charge pump 510 pulls the voltage $V_{out}$ at the electrowetting lens downward. On the other hand, if the electrowetting lens transitions from being coupled to charge pump 510 to being coupled to charge pump 500, then reset switch 816 can be closed to set the voltage of $V_{sense1}$ to be $V_{ss}$, and the reset switch 816 can then be reopened to allow $V_{sense1}$ to drift upwards as charge pump 500 pulls the voltage $V_{out}$ at the electrowetting lens upward.

As $V_{sense1}$ tracks the electrowetting lens voltage $V_{out}$ by drifting upward or downward, the multiplexer 830, ADC 840, and controller 850 can be configured to measure $V_{sense1}$ and determine $V_{out}$ based on the measurement. In particular, the multiplexer 830 can pass the $V_{sense1}$ voltage to the ADC 840, which can convert $V_{sense1}$ into a digital signal. Based on the converted digital signal, the controller 850 can determine the value of $V_{out}$. The controller 850 can be configured to repeatedly monitor the value of $V_{out}$ over time by taking recurring measurements of $V_{sense1}$.

The ADC 840 may be configured to receive analog signals within a limited voltage range, such that the controller 850 may only determine accurate measurements of $V_{out}$ while $V_{sense1}$ remains within the limited voltage range of the ADC 840. Further, the voltage-sensing circuit 800 may have a number of parasitic leakage sources due to imperfections in various circuit elements that cause the value of $V_{sense1}$ to drift out of the limited voltage range of the ADC 840. To account for this, the voltage-sensing circuit 800 can be configured to switch to monitoring $V_{out}$ using the second capacitive voltage divider 820 before $V_{sense1}$ drifts out of the voltage range of the ADC 840.

For example, once the controller 850 has been monitoring $V_{sense1}$ for a predetermined period of time, the controller 850 can cause the multiplexer 830 to transition from passing $V_{sense1}$ to the ADC 840 to passing $V_{sense2}$ to the ADC 840. The predetermined period of time can depend on the leakage rate of the voltage-sensing circuit 800. For instance, if the parasitic leakage is low, then the predetermined period of time may be longer, and if the parasitic leakage is high, then the predetermined period of time may be shorter. In any case, the predetermined period of time may be short enough that the parasitic leakage does not cause $V_{sense1}$ to drift out of the limited voltage range of the ADC 840.

Before the controller 850 causes the multiplexer 830 to transition to passing $V_{sense2}$ to the ADC 840, $V_{sense2}$ can be set to a baseline voltage. In particular, $V_{sense2}$ can be set to $V_{mid}$ by closing switch 822. The value of $V_{mid}$ may be a voltage that falls within the limited voltage range of the ADC 840. For instance, $V_{mid}$ may be a voltage that is halfway between a minimum voltage and a maximum voltage of the limited voltage range of the ADC 840.

Once $V_{sense2}$ is set to the $V_{mid}$ voltage, the controller 850 can take a baseline measurement of $V_{sense2}$ and the switch 822 can be reopened to allow $V_{sense2}$ to be pulled upward or downward as $V_{out}$ increases or decreases. The controller 850 can then continue to measure $V_{sense2}$ and determine $V_{out}$ based on the measurement. After the predetermined time has elapsed, $V_{sense1}$ can be set to the $V_{mid}$ baseline by temporarily closing switch 812, and the controller 850 can cause the multiplexer 830 to transition back to passing $V_{sense1}$ to the ADC 840. The controller 850 can continue this process of switching back and forth between measuring $V_{sense1}$ and $V_{sense2}$, thereby preventing parasitic leakages from causing the voltages from drifting outside of the voltage range of the ADC 840.

In some examples, the capacitive voltage dividers 810, 820 can further include one or more resistors coupled in parallel to the capacitors of the voltage dividers. The resistors can be chosen such that the ratio of the resistance of the resistors forms a resistive voltage divider that steps down the output voltage $V_{out}$ to a voltage that falls within the voltage range of the ADC 840. Further, the resistors can have a substantially large resistance in order to minimize the loading current of the resistors and reduce power consumption of the circuit 800. With the resistors forming resistive voltage dividers in parallel with the capacitive voltage dividers 810, 820, the $V_{sense1}$ and $V_{sense2}$ voltages can have better DC stability. For instance, the capacitors of the capacitive voltage dividers 810, 820 can allow the voltage at $V_{sense1}$ or $V_{sense2}$ to rapidly change as the output voltage $V_{out}$ changes, while the resistors of the resistive voltage dividers can help hold the voltage at $V_{sense1}$ or $V_{sense2}$ within the voltage range of the ADC 840.

Further, the voltage-sensing circuit 800 can be configured to adjust the input voltage $V_{in}$ provided to the charge pump based on the measured output voltage $V_{out}$ of the charge pump. For instance, because the output voltage $V_{out}$ of the charge pump is proportional to the input voltage $V_{in}$ of the charge pump, if the measured $V_{out}$ is too high, then the controller 850 can cause the DAC 860 to decrease the value of $V_{in}$ that is supplied to the charge pump. On the other hand, if the measured $V_{out}$ is too low, then the controller can cause the DAC 860 to increase the value of $V_{in}$ that is supplied to the charge pump.

Figure 9:
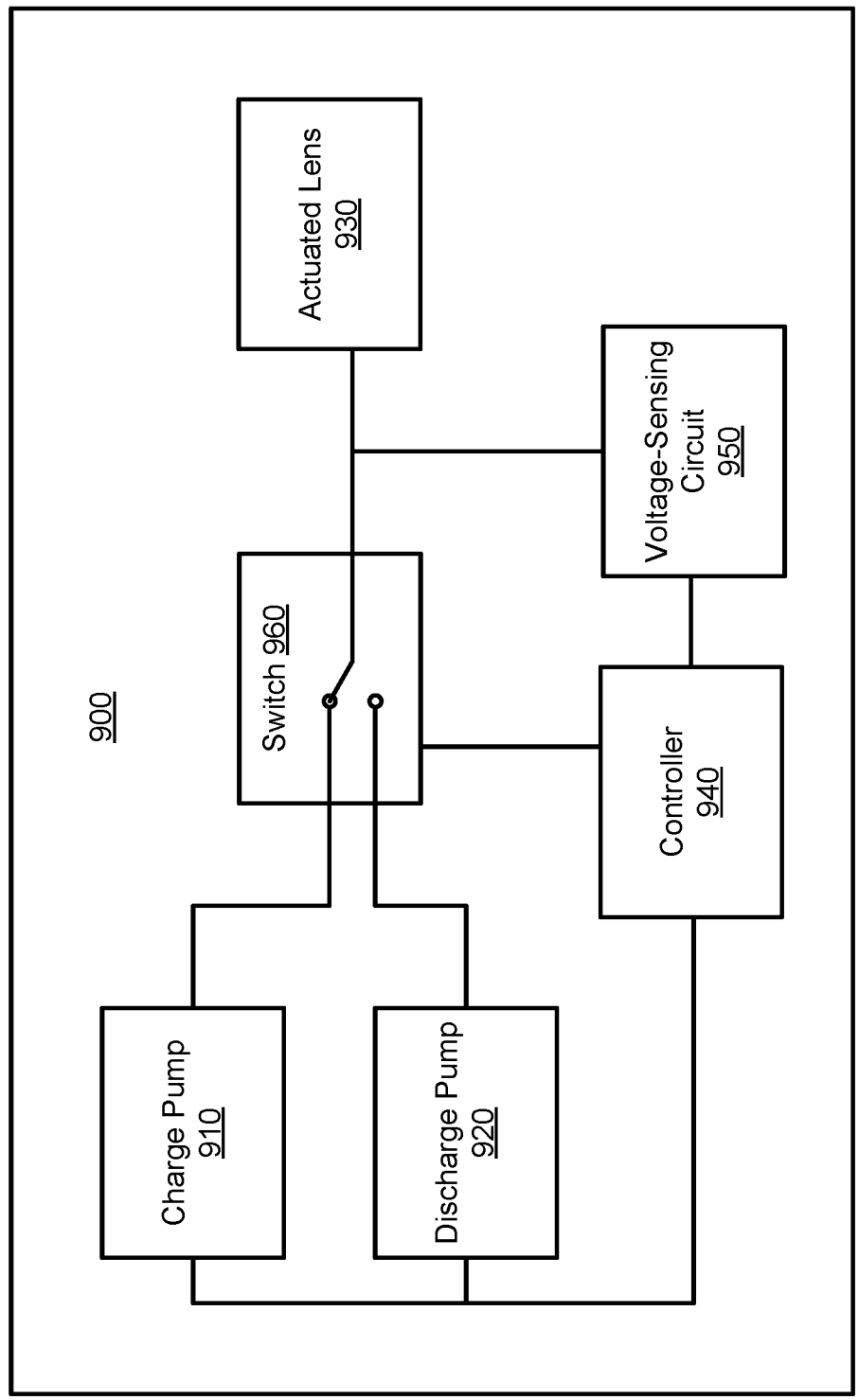
FIG. 9 is another block diagram of an example eye-implantable or eye-mountable system.

FIG. 9 is another block diagram of an example eye-implantable or eye-mountable system 900 in accordance with the above description. The system includes a charge pump 910, a discharge pump 920, an actuated lens 930, a controller 940, and a voltage-sensing circuit 950, and a switch 960 configured to electrically couple the charge pump 910 or the discharge pump 920 to the actuated lens 930.

The charge pump 910 can be similar to or the same as the charge pump 500 shown in FIG. 5A, and the discharge pump 920 can be similar to or the same as the charge pump 510 shown in FIG. 5B. For instance, the charge pump 910 can be operable to convert an input voltage to a larger positive voltage, and the discharge pump 920 can be operable to convert an input voltage to a larger negative voltage. As such, when the charge pump 910 is electrically coupled to the actuated lens 930, the charge pump 910 can pump positive charge to the actuated lens 930, and when the discharge pump 920 is electrically coupled to the actuated lens 930, the discharge pump 920 can pump positive charge away from the actuated lens 930.

The actuated lens 930 can be similar to or the same as the electrowetting lens 200 shown in FIGS. 2A and 2B. For instance, the actuated lens 930 can have a first electrode in contact with a first fluid and a second electrode in contact with a second fluid. Adjusting a voltage across the first and second electrodes can adjust a shape of the first and second fluids, thereby adjusting an optical power of the actuated lens 930. As such, the optical power of the actuated lens 930 can be adjusted by pumping charge to the electrodes of the actuated lens 930 (e.g., charging the actuated lens 930) in order to increase the voltage across the electrodes or by pumping charge away from the electrodes of the actuated lens 930 (e.g., discharging the actuated lens 930) in order to decrease the voltage across the electrodes. In particular, the controller 940 can charge the actuated lens 930 by causing the switch 960 to connect an output of the charge pump 910 to the electrodes of the actuated lens 930, and after charging the actuated lens 930 the controller 940 can discharge the actuated lens 930 by causing the switch 960 to connect an output of the discharge pump 920 to the electrodes of the actuated lens 930. By charging and discharging the actuated lens 930, the controller 940 can adjust an optical power of the actuated lens 930, thereby adjusting an optical power available for vision when the actuated lens 930 is implanted in or mounted on an eye.

The switch 960 can take various forms. For instance, the switch 960 can include one or more transistors, such as a MOSFET or a BJT, and the controller 940 can toggle the switch 960 by applying a voltage to a gate or base terminal of the transistor. Other examples are possible as well.

In line with the discussion above, in some examples, the system 900 may not include the switch 960. For instance, the charge pump 910 and the discharge pump 920 can be electrically coupled to the actuated lens 930 at the same time. As such, the controller 940 can activate the charge pump 910 and deactivate the discharge pump 920 to charge the actuated lens 930. Similarly, the controller 940 can activate the discharge pump 920 and deactivate the charge pump 910 to discharge the actuated lens 930. Excluding the switch 960 can allow the system 900 to operate the charge pump 910 and discharge pump 920 using standard low-voltage CMOS processes without using high voltage electronics that could increase the size and complexity of the system.

The voltage-sensing circuit 950 can be similar to or the same as the voltage sensing circuit 800 shown in FIG. 8. For instance, the voltage-sensing circuit 950 can include a first capacitive voltage divider and a second capacitive voltage divider. The controller 940 can carry out a voltage-measurement process using the voltage sensitive circuit 950. For instance, in line with the discussion above, the controller 940 can control a multiplexer of the voltage-sensing circuit 950 to couple the first capacitive voltage divider to the actuated lens 930 such that the voltage supplied to the actuated lens 930 is divided across the first capacitive voltage divider. The controller 940 can then determine the voltage supplied to the actuated lens 930 based on the voltage output of the capacitive voltage divider. If the determined voltage is too low, then the controller 940 can increase the voltage by increasing the input voltage to the charge pump 910. If the determined voltage is too high, then the controller 940 can lower the voltage by decreasing the input voltage to the charge pump 910 and/or by toggling the switch 960 to couple the discharge pump 920 to the actuated lens 930.

Figure 10:
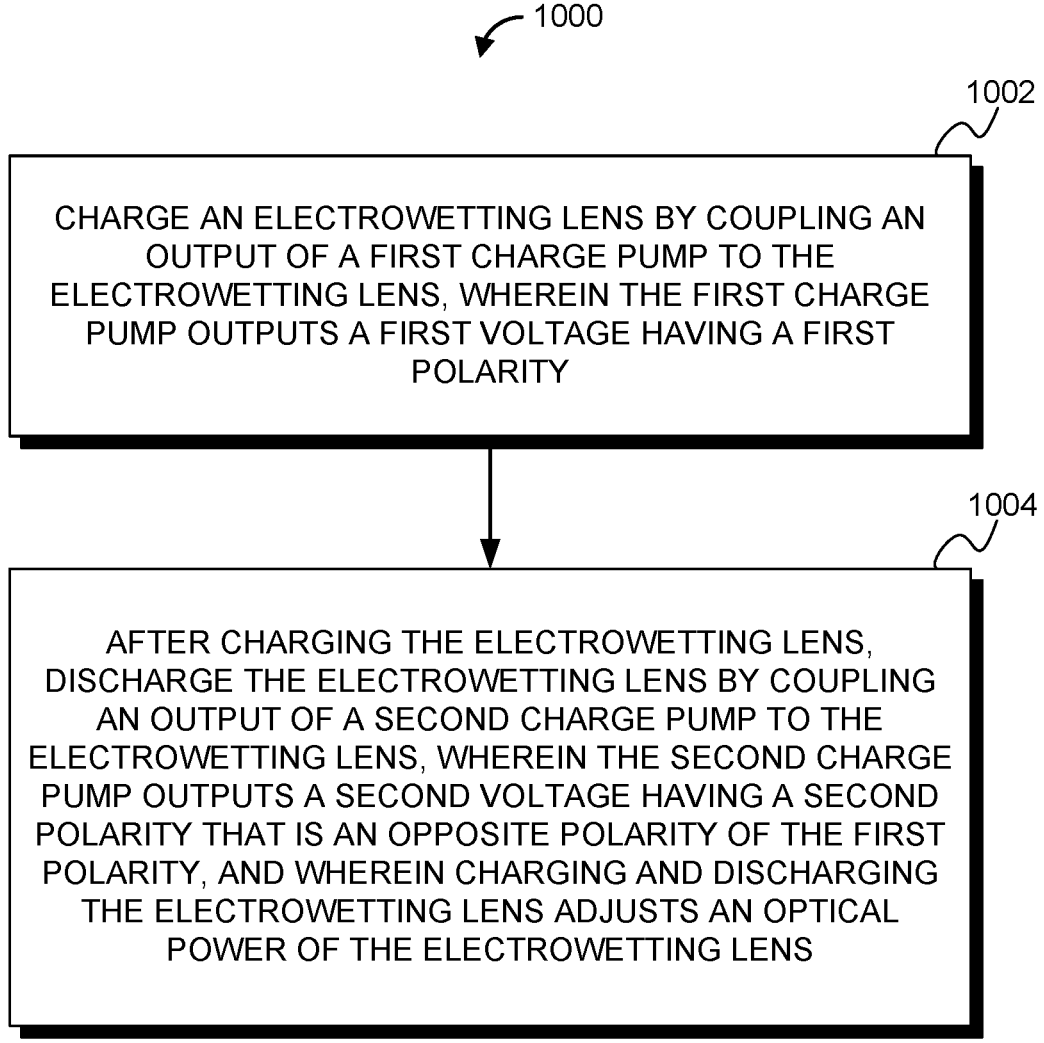
FIG. 10 is a flowchart of an example process.

In order to account for leakage current in the voltage-sensing circuit 950, the controller 940 can, after a duration of time, uncouple the first capacitive voltage divider from the actuated lens 930 and the second capacitive voltage divider to the actuated lens 930. The controller 940 can continue to periodically switch the coupling between the first capacitive voltage divider and the second capacitive voltage divider. In some examples, the duration of time is based on a charge leakage rate of one or more capacitors of the first capacitive voltage divider or the second capacitive voltage divider V. Example Methods FIG. 10 is a flowchart of a method 1000 for driving an electrowetting lens of an eye-implantable or eye-mountable device. The electrowetting lens can take various forms as described herein and can include, for instance, (i) a polymeric material that is permeable to water in an aqueous humor of the eye, (ii) a lens chamber, at least a portion of which is formed from the polymeric material, (iii) a first fluid that is disposed within the lens chamber and that has an osmolality corresponding to an osmolality of the aqueous humor, (iv) a second fluid that is disposed within the lens chamber, that is immiscible with the first fluid, and that differs from the first fluid with respect to refractive index, (v) a first electrode that is disposed on an internal surface of the lens chamber in contact with the first fluid, and (vi) a second electrode that includes a dielectric coating and that is disposed on an internal surface of the lens chamber in contact with at least one of the first fluid or the second fluid.

At block 1002, the method 1000 includes charging the electrowetting lens by coupling an output of a first charge pump to the electrowetting lens, wherein the first charge pump outputs a first voltage having a first polarity. For example, the first charge pump could be a Dickson charge pump, as shown in FIG. 5A, configured to output a positive voltage (e.g., 20V or above) that is greater in magnitude than typical digital voltages. The output of the first charge pump can be coupled to the electrowetting lens by coupling the first charge pump to the first and second electrodes of the electrowetting lens.

At block 1004, the method 1000 includes, after charging the electrowetting lens, discharging the electrowetting lens by coupling an output of a second charge pump to the electrowetting lens, wherein the second charge pump outputs a second voltage having a second polarity that is an opposite polarity of the first polarity, and wherein charging and discharging the electrowetting lens adjusts an optical power of the electrowetting lens. For example, the second charge pump could be a Dickson charge pump, as shown in FIG. 5B, configured to output a negative voltage (e.g., −20V or below) that is greater in magnitude than typical digital voltages. The output of the second charge pump can be coupled to the electrowetting lens by decoupling the first charge pump from the first and second electrodes of the electrowetting lens and coupling the second charge pump to the electrodes. In this manner, the second charge pump can discharge the electrowetting lens by pumping charge away from the electrowetting lens, thereby increasing a rate of discharge of the electrowetting lens. In line with the discussion above, the processes of charging and discharging the electrowetting lens adjusts the shape of the fluids within the electrowetting lens and thus adjusts an optical power of the electrowetting lens.

The method 1000 could include additional steps or elements in addition to those depicted in FIG. 10. For example, the method 1000 could include using a voltage-sensing circuit to measure an output voltage of at least one of the first charge pump or the second charge pump. In line with the discussion above, the voltage-sensing circuit can include a first capacitive voltage divider and a second capacitive voltage divider. A voltage measurement process can thus include coupling an output of the first charge pump or the second charge pump to the first capacitive voltage divider, determining that the output of the first charge pump or the second charge pump has been coupled to the first capacitive voltage divider for a duration of time, and responsive to determining that the output of the first charge pump or the second charge pump has been coupled to the first capacitive voltage divider for the duration of time, (i) uncoupling the output of the first charge pump or the second charge pump from the first capacitive voltage divider and (ii) coupling the output of the first charge pump or the second charge pump to the second capacitive voltage divider. In some examples, the duration of time is based on a charge leakage rate of one or more capacitors of the first capacitive voltage divider or the second capacitive voltage divider.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   an electrowetting lens;
   a first charge pump that outputs a first voltage having a first polarity;
   a second charge pump that outputs a second voltage having a second polarity, wherein the second polarity is an opposite polarity of the first polarity; and
   a controller operable to (i) charge the electrowetting lens by coupling the first charge pump to the electrowetting lens and (ii) after charging the electrowetting lens, discharge the electrowetting lens by coupling the second charge pump to the electrowetting lens, wherein charging and discharging the electrowetting lens adjusts an optical power of the electrowetting lens.

2. The system of claim 1, wherein the electrowetting lens comprises:
   a first fluid disposed in the lens;
   a second fluid disposed in the lens, wherein the second fluid is immiscible with the first fluid, and wherein a refractive index of the second fluid differs from a refractive index of the first fluid;
   a first electrode in contact with the first fluid; and
   a second electrode in contact with at least one of the first fluid or the second fluid.

3. The system of claim 2, wherein coupling the first charge pump to the electrowetting lens comprises coupling the first charge pump to the first and the second electrodes of the electrowetting lens, and wherein coupling the second charge pump to the electrowetting lens comprises coupling the second charge pump to the first and second electrodes of the electrowetting lens.

4. The system of claim 1, further comprising a voltage-sensing circuit for measuring at least one of the first voltage output by the first charge pump or the second voltage output by the second charge pump, wherein the voltage-sensing circuit comprises:
   a first capacitive voltage divider; and
   a second capacitive voltage divider.

5. The system of claim 1, wherein the controller is further operable to perform a voltage measurement process comprising:
   coupling an output of the first charge pump or the second charge pump to the first capacitive voltage divider;
   determining that the output of the first charge pump or the second charge pump has been coupled to the first capacitive voltage divider for a duration of time; and
   responsive to determining that the output of the first charge pump or the second charge pump has been coupled to the first capacitive voltage divider for the duration of time, (i) uncoupling the output of the first charge pump or the second charge pump from the first capacitive voltage divider and (ii) coupling the output of the first charge pump or the second charge pump to the second capacitive voltage divider.

6. The system of claim 5, wherein the duration of time is based on a charge leakage rate of one or more capacitors of the first capacitive voltage divider.

7. The system of claim 1, wherein the system is an eye-implantable system, and wherein adjusting the optical power of the electrowetting lens adjusts an optical power available for vision when the system is implanted in an eye.

8. The system of claim 1, wherein the system is an eye-mountable system, and wherein adjusting the optical power of the electrowetting lens adjusts an optical power available for vision when the system is mounted on an eye.

9. The system of claim 1, wherein the first polarity is a positive polarity and the second polarity is a negative polarity.

10. The system of claim 1, wherein at least one of the first charge pump or the second charge pump is a Dickson charge pump.

11. The system of claim 1, wherein at least one of the first charge pump or the second charge pump comprises a plurality of PIN diodes.

12. The system of claim 1, further comprising:
   a voltage-sensing circuit comprising a first capacitive voltage divider having a first voltage output, a second capacitive voltage divider having a second voltage output, a multiplexer, and an analog-to-digital converter (ADC),
   wherein the controller is further operable to control the voltage-sensing circuit to measure voltages output by the first charge pump and the second charge pump.

13. A system comprising:
   an electrowetting lens;
   a first charge pump coupled to the electrowetting lens, wherein the first charge pump can pump charge to the electrowetting lens;
   a second charge pump coupled to the electrowetting lens, wherein the second charge pump can pump charge away from the electrowetting lens; and
   a controller operable to (i) charge the electrowetting lens by activating the first charge pump and (ii) after charging the electrowetting lens, discharge the electrowetting lens by deactivating the first charge pump and activating the second charge pump, wherein charging and discharging the electrowetting lens adjusts an optical power of the electrowetting lens.

14. The system of claim 13, wherein the electrowetting lens comprises:
   a first fluid disposed in the lens;
   a second fluid disposed in the lens, wherein the second fluid is immiscible with the first fluid, and wherein a refractive index of the second fluid differs from a refractive index of the first fluid;
   a first electrode in contact with the first fluid; and
   a second electrode in contact with at least one of the first fluid or the second fluid, wherein the first charge pump and the second charge pump are coupled to the first and the second electrodes of the electrowetting lens.

15. The system of claim 13, wherein an output of the first charge pump and an output of the second charge pump are electrically coupled at an output terminal.

16. The system of claim 15, wherein the controller is further operable to perform a voltage measurement process comprising:
   coupling the output terminal to the first capacitive voltage divider;
   determining that the output terminal has been coupled to the first capacitive voltage divider for a duration of time; and
   responsive to determining that the output terminal has been coupled to the first capacitive voltage divider for the duration of time, (i) uncoupling the output terminal from the first capacitive voltage divider and (ii) coupling the output terminal to the second capacitive voltage divider.

17. The system of claim 16, wherein the duration of time is based on a charge leakage rate of one or more capacitors of the first capacitive voltage divider.

18. The system of claim 13, further comprising:
   a voltage-sensing circuit comprising a first capacitive voltage divider having a first voltage output, a second capacitive voltage divider having a second voltage output, a multiplexer, and an analog-to-digital converter (ADC),
   wherein the controller is further operable to control the voltage-sensing circuit to measure voltages output by the first charge pump and the second charge pump.

* * * * *